United States Patent
Tso et al.

(10) Patent No.: US 10,232,019 B2
(45) Date of Patent: *Mar. 19, 2019

(54) METHOD OF TREATING HYPERGLYCEMIC DISORDERS USING APOLIPOPROTEIN AIV

(71) Applicant: University of Cincinnati, Cincinnati, OH (US)

(72) Inventors: Patrick Tso, Cincinnati, OH (US); Fei Wang, Cincinnati, OH (US); Sean Davidson, Cincinnati, OH (US); Stephen Woods, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/416,541

(22) PCT Filed: Nov. 21, 2012

(86) PCT No.: PCT/US2012/066334
§ 371 (c)(1),
(2) Date: Jan. 22, 2015

(87) PCT Pub. No.: WO2014/018079
PCT Pub. Date: Jan. 30, 2014

(65) Prior Publication Data
US 2015/0182591 A1    Jul. 2, 2015

Related U.S. Application Data

(60) Provisional application No. 61/675,549, filed on Jul. 25, 2012.

(51) Int. Cl.
| *A61K 38/00* | (2006.01) |
| *A61P 3/08* | (2006.01) |
| *A61P 3/10* | (2006.01) |
| *A61K 38/16* | (2006.01) |
| *C07K 1/00* | (2006.01) |
| *C07K 14/00* | (2006.01) |
| *C07K 16/00* | (2006.01) |
| *C07K 17/00* | (2006.01) |
| *A61K 38/22* | (2006.01) |
| *A61K 38/17* | (2006.01) |
| *C07K 14/775* | (2006.01) |

(52) U.S. Cl.
CPC .......... *A61K 38/22* (2013.01); *A61K 38/1709* (2013.01); *C07K 14/775* (2013.01)

(58) Field of Classification Search
None
See application file for complete search history.

(56) References Cited

U.S. PATENT DOCUMENTS 9,051,394 B2    6/2015 Tso et al.
9,266,941 B2 *  2/2016 Tso .................. A61K 38/1709
2004/0029784 A1* 2/2004 Hathaway ............. A61K 38/26
                                                             514/4.8
2010/0267052 A1   10/2010 Gelber et al.
2014/0005107 A1    1/2014 Tso et al.
2015/0011469 A1    1/2015 Tso et al.
2015/0150939 A1*   6/2015 Pinkosky ........... A61K 38/1709
                                                             514/7.4

FOREIGN PATENT DOCUMENTS

| CN | 1668645 A | 9/2005 |
| WO | 1993/015198 A1 | 8/1993 |
| WO | 1994/027629 A1 | 12/1994 |
| WO | 2003/097696 A1 | 11/2003 |
| WO | 2009/116861 A2 | 9/2009 |
| WO | 2010/060387 A1 | 6/2010 |
| WO | 2012/100010 A1 | 7/2012 |
| WO | 2013/109342 A1 | 7/2013 |
| WO | 2014/018763 A2 | 1/2014 |

OTHER PUBLICATIONS

American Diabetes Association, "Hyperglycemia", available online at http://www.diabetes.org/living-with-diabetes/treatment-and-care/blood-glucose-control/hyperglycemia.html, 4 pages (accessed on May 15, 2016).*
Barbeiri et al., Annu. Rev. Med. 42:99-104 (1991) (Year: 1991).*
Database Biosis, [Online] (2002), "Physiology of the small intestine in the glycemic control and the treatment of diabetes mellitus".
Elshourbagy et al., "The Nucleotide and Amino Acid Sequence of Human Apolipoprotein A-IV mRNA and the Close Linkage of its Gene to the Genes of Apolipoproteins A-I and C-III," J. Biol. Chem. 261:1998-2002 (1986).
Fei, Wang et al., "Apolipoprotein A-IV improves glucose homeostasis by enhancing insulin secretion", Proceedings of the National Academy of Sciences—PNAS, 109(24): 9641-9646 (2012).
Fujimoto, K. et al., "Suppression of Food Intake by Apoliproprotein A-IV is Mediated through the Central Nervous System in Rats," J. Clin. Invest., 9:1830-1833 (1993).

(Continued)

*Primary Examiner* — James H Alstrum-Acevedo
*Assistant Examiner* — Thea D' Ambrosio
(74) *Attorney, Agent, or Firm* — Dinsmore & Shohl LLP

(57) ABSTRACT

Methods for treating hyperglycemia disorders in a subject in need thereof and pharmaceutical compositions for the treatment of hyperglycemia disorders are disclosed. The methods include administering an effective amount of apolipoprotein A-IV to the subject. Also disclosed are methods for substantially restoring glucose tolerance in a subject in need thereof to a normal level and methods for lowering blood glucose levels in a subject having hyperglycemic disorders, including insulin resistant disorders, such as prediabetes, metabolic syndrome, polycystic ovary disease, type A syndrome, gestational diabetes, and endocrine conditions associated with hyperglycemia, including Cushing's Disease, glucagon excess (glucagon secreting tumors) and acromegaly.

10 Claims, 13 Drawing Sheets
Specification includes a Sequence Listing.

(56) References Cited

OTHER PUBLICATIONS

Glatzle J, et al., Apolipoprotein A-IV stimulates duodenal vagal afferent activity to inhibit gastric motility via a CCK1 pathway, Am J Physiol Regul Integr Comp Physiol. 2004;287(2):R354-9.
Mahley et al., "Plasma Lipoproteins: apolipoprotein and function," J. Lipid Res. 25:1277-1294 (1984).
NCBI Database; Accession No. P06727.3; GI: 93163358, Mar. 7, 2006.
Okumura T, et al., Apolipoprotein A-IV acts in the brain to inhibit gastric emptying in the rat, Am J Physiol. 1996; 270(1 Pt 1):G49-53.
Okumura T, et al: "Physiology of the small intestine in the glycemic control and the treatment of diabetes mellitus", Folia Pharmacologica Japonica, 120(1), 2002, pp. 29-31.
Suen, et al: "The potential of incretin-based therapies in type 1 diabetes", Drug Discovery Today, vol. 17. No. 1, (2012), pp. 89-95.
University of Cincinnati Academic Health Center, "Diabetes Drug Target Identified", Health News, May 21, 2012, URL: http://healthnews.uc.edu/pdf/UC_HealthNews_20334.pdf, the whole document.
Van Belle, et al: "Type 1 diabetes: etiology, immunology, and therapeutic strategies", Reviews Physiological 91(1), 2011, pp. 79-118.
International Search Report and Written Opinion issued in PCT/US2012/066334, (dated May 24, 2013).
JP Office Action to corresponding Application No. JP 2015-524242, (dated Jun. 6, 2016).
Nicolas Duverger et al, "Functional characterization of human recombinant apolipoprotein AIV produced in *Escherichia coli*," Eur. J. Biochem, 201, 373-383 (1991).

\* cited by examiner

EVSADQVATVMWDYFSQLSNNAKEAVEHLQKSELTQQLNALFQDKLGEVNTYAGDLQ
KKLVPFATELHERLAKDSEKLKEEIGKELEELRARLLPHANEVSQKIGDNLRELQQRLEP
YADQLRTQVNTQAEQLRRQLTPYAQRMERVLRENADSLQASLRPHADELKAKIDQNVE
ELKGRLTPYADEFKVKIDQTVEELRRSLAPYAQDTQEKLNHQLEGLTFQMKKNAEELK
ARISASAEELRQRLAPLAEDVRGNLRGNTEGLQKSLAELGGHLDQQVEEFRRRVEPYGE
NFNKALVQQMEQLRQKLGPHAGDVEGHLSFLEKDLRDKVNSFFSTFKEKESQDKTLSLP
ELEQQQEQQQEQQQEQVQMLAPLES

SEQ ID NO. 1

FIG. 15

EVTSDQVANVVWDYFTQLSNNAKEAVEQFQKTDVQQLSTLFASTYADGVHNKLVPFV
VQLSGHLAQETERVKEEIKKELEDLRDRKTQTFGENMQKLQEHLKPYAVDLQDQINTQ
TQEMKLQLTPYIQRMQTTIKENVDNLHTSMMPLATNLKDKFNRNMEELKGHLTPRANE
LKATIDQNLEDLRRSLAPLTVGVQEKLNHQMEGLAFQMKKNAEELQTKVSAKIDQLQK
NLAPLVEDVQSKVKGNTEGLQKSLEDLNRQLEQQVEEFRRTVEPMGEMFNKALVQQLE
QFRQQLGPNSGEVESHLSFLEKSLREKVNSFMSTLEKKGSPDQPQALPLPEQAQEQAQE
QAQEQVQPKPLES

SEQ ID NO. 2

FIG. 16

GEVSADQVATVMWDYFSQLSNNAKEAVEHLQKSELTQQLNALFQDKLGEVNTYAGDL
QKKLVPFATELHERLAKDSEKLKEEIGKELEELRARLLPHANEVSQKIGDNLRELQQRLE
PYADQLRTQVNTQAEQLRRQLTPYAQRMERVLRENADSLQASLRPHADELKAKIDQNV
EELKGRLTPYADEFKVKIDQTVEELRRSLAPYAQDTQEKLNHQLEGLTFQMKKNAEEL
KARISASAEELRQRLAPLAEDVRGNLRGNTEGLQKSLAELGGHLDQQVEEFRRRVEPYG
ENFNKALVQQMEQLRQKLGPHAGDVEGHLSFLEKDLRDKVNSFFSTFKEKESQDKTLS
LPELEQQQEQQQEQQQEQVQMLAPLES

SEQ ID NO. 3

FIG. 17

X₁EVSADQVATVMWDYFSQLSNNAKEAVEHLQKSELTQQLNALFQDKLGEVNTYAGD
LQKKLVPFATELHERLAKDSEKLKEEIGKELEELRARLLPHANEVSQKIGDNLRELQQRL
EPYADQLRTQVNTQAEQLRRQLTPYAQRMERVLRENADSLQASLRPHADX₂LKAKIDQ
NVEELKGRLTPYADEFKVKIDQTVEELRRSLAPYAQDTQEKLNHQLEGLTFQMKKNAE
ELKARISASAEELRQRLAPLAEDVRGNLRGNTEGLQKSLAELGGHLDQQVEEFRRRVEP
YGENFNKALVQQMEQLRQKLGPHAGDVEGHLSFLEKDLRDKVNSFFSTFKEKESQDKX
₃LSLPELEQQQEQX₃QEQQQEQVQMLAPLES

X₁ is G, A, V or absent

X₂ is E or K

X₃ is T or S

X₄ is Q or H

SEQ ID NO. 4

FIG. 18

```
GTCAGTGCTGACCAGGTGGCCACAGTGATGTGGGACTACTTCAGCCAGCTGAGCAA
CAATGCCAAGGAGGCCGTGGAACATCTCCAGAAATCTGAACTCACCCAGCAACTCA
ATGCCCTCTTCCAGGACAAACTTGGAGAAGTGAACACTTACGCAGGTGACCTGCAG
AAGAAGCTGGTGCCCTTTGCCACCGAGCTGCATGAACGCCTGGCCAAGGACTCGGA
GAAACTGAAGGAGGAGATTGGGAAGGAGCTGGAGGAGCTGAGGGCCCGGCTGCTG
CCCCATGCCAATGAGGTGAGCCAGAAGATCGGGGACAACCTGCGAGAGCTTCAGCA
GCGCCTGGAGCCCTACGCGGACCAGCTGCGCACCCAGGTCAACACGCAGGCCGAGC
AGCTGCGGCGCCAGCTGACCCCCTACGCACAGCGCATGGAGAGAGTGCTGCGGGAG
AACGCCGACAGCCTGCAGGCCTCGCTGAGGCCCCACGCCGACGAGCTCAAGGCCAA
GATCGACCAGAACGTGGAGGAGCTCAAGGGACGCCTTACGCCCTACGCTGACGAAT
TCAAAGTCAAGATTGACCAGACCGTGGAGGAGCTGCGCCGCAGCCTGGCTCCCTAT
GCTCAGGACACGCAGGAGAAGCTCAACCACCAGCTTGAGGGCCTGACCTTCCAGAT
GAAGAAGAACGCCGAGGAGCTCAAGGCCAGGATCTCGGCCAGTGCCGAGGAGCTG
CGGCAGAGGCTGGCGCCCTTGGCCGAGGACGTGCGTGGCAACCTGAGGGGCAACAC
CGAGGGGCTGCAGAAGTCACTGGCAGAGCTGGGTGGGCACCTGGACCAGCAGGTGG
AGGAGTTCCGACGCCGGGTGGAGCCCTACGGGGAAAACTTCAACAAAGCCCTGGTG
CAGCAGATGGAACAGCTCAGGCAGAAACTGGGCCCCATGCGGGGACGTGGAAG
GCCACCTGAGCTTCCTGGAGAAGGACCTGAGGGACAAGGTCAACTCCTTCTTCAGC
ACCTTCAAGGAGAAAGAGAGCCAGGACAAGACTCTCTCCCTCCCTGAGCTCGAGCA
ACAGCAGGAACAGCAGCAGGAGCAGCAGCAGGAGCAGGTGCAGATGCTGGCCCCT
TTGGAGAGC
```

SEQ ID NO. 5

FIG. 19

METHOD OF TREATING HYPERGLYCEMIC DISORDERS USING APOLIPOPROTEIN AIV

RELATED APPLICATIONS

This application is a 35 U.S.C. § 371 national stage filing of International Application No. PCT/US2012/066334, filed on Nov. 21, 2012, which claims priority to U.S. Provisional Patent Application No. 61/675,549, filed on Jul. 25, 2012. The contents of the foregoing applications are hereby incorporated by reference in their entirety.

TECHNICAL FIELD

The present disclosure relates to a method of treating conditions related hyperglycemia. More particularly, the present disclosure relates to a method of treating hyperglycemic disorders, including insulin resistant and endocrine disorders, by administering an effective amount of apolipoprotein A-IV.

BACKGROUND

The occurrence of diabetes is widespread, with approximately 8% of the population in the United States suffering from diabetes. Diabetes is a chronic disease characterized by high blood sugar due to the body's inability to effectively produce and/or use insulin. Diabetes can lead to a variety of physical complications, including but not limited to renal failure, blindness, nerve damage, heart disease, sleep apnea, and celiac disease. For example, in the United States, diabetes is the leading cause of renal failure, blindness, amputation, stroke, and heart attack. Also in the United States, diabetes is the sixth leading cause of death and has been shown to reduce the life expectancy of middle-aged adults by about five to ten years.

The most common form of diabetes is type two diabetes mellitus which is associated with hyperglycemia, insulin resistance, β-cell dysfunction, and dysregulated hepatic gluconeogenesis. Persons suffering from type two diabetes experience a loss of glucose-stimulated insulin secretion related to the impaired release of stored insulin granules from β-cells in the first phase of insulin secretion. In the second phase of insulin secretion, persons suffering from type two diabetes experience a gradual loss of the ability to actively synthesize insulin in response to glucose stimuli.

In addition to type II diabetes, there are a number of related conditions defined by hyperglycemia that are also increasing in the general population. For example, from 2005 to 2008, 35 percent of U.S. adults ages 20 years or older had prediabetes (defined by a fasting glucose or A1C levels; see CDC). As such, new therapies for effectively treating conditions related to hyperglycemia are needed.

SUMMARY OF INVENTION

The present disclosure is based on the surprising discovery that apolipoprotein A-IV is effective for treating disorders characterized by hyperglycemia (or hyperglycemia disorders).

Apolipoprotein A-IV is a key gut hormone which contributes to post-prandial glucose tolerance and acts as a previously unappreciated mediator in the improvement of glucose tolerance. Accordingly, in one embodiment, methods of treating a hyperglycemia disorder in a subject in need thereof are disclosed. In one embodiment, methods of treating hyperglycemia disorders including insulin resistant disorders or endocrine disorders associated with hyperglycemia in a subject in need thereof are disclosed. In one embodiment, methods of treating endocrine disorders associated with hyperglycemia including Cushing's disease, glucagon secreting tumors, glucagon excess, and acromegaly in a subject in need thereof are disclosed. In another embodiment, methods of treating hyperglycemia in a subject having polycystic ovary disease are disclosed. In another embodiment, methods of treating hyperglycemia in a subject having an insulin resistant disorder selected from the group consisting of prediabetes, metabolic syndrome, polycystic ovary disease, type A syndrome, and gestational diabetes are disclosed. The method comprises administering to the subject an effective amount of an apolipoprotein A-IV or a biologically active analogue thereof having at least 90, 95, 96, 97, 98 or 99% identity to the apolipoprotein A-IV.

In another embodiment, a pharmaceutical composition comprising apolipoprotein A-IV is disclosed. The pharmaceutical composition comprises an apolipoprotein A-IV or a biologically active analogue thereof having at least 90, 95, 96, 97, 98 or 99% identity to the apolipoprotein A-IV formulated for administration to a subject for the treatment of hyperglycemia disorders.

In yet another embodiment, a method for substantially restoring glucose tolerance in a subject in need thereof to a normal level is disclosed. The method comprises administering to the subject an effective amount of an apolipoprotein A-IV or a biologically active analogue thereof having at least 90, 95, 96, 97, 98 or 99% identity to an apolipoprotein A-IV, for example, by systemic administration of the apolipoprotein A-IV or the biologically active analogue thereof.

In yet still another embodiment, a method for lowering blood glucose level in a subject in need thereof is disclosed. The method comprises administering to the subject an effective amount of apolipoprotein A-IV or a biologically active analogue thereof having at least 90, 95, 96, 97, 98 or 99% identity to the apolipoprotein A-IV to the subject in need, for example, by systemic administration. An "effective amount" is as described below and includes, for example, about 0.25 to 2 µg/g of the apoA-IV or the biologically active analogue thereof. In one embodiment the effective amount is about 0.1 mg/kg to 25 mg/kg. In another embodiment, the effective amount is a fixed dose of about 1 to 1000 mg. In a further embodiment, the effective amount is a fixed dose of about 1 to 10 mg.

In a further embodiment, the apolipoprotein A-IV, or biologically active analogue thereof, is non-glycosylated.

In one embodiment, the methods and compositions disclosed herein include an apoA-IV protein comprising an amino acid sequence as set forth in any one of SEQ ID NOs: 1, 3, 4 or 6-51, or biologically active fragments thereof. In one embodiment, the methods and compositions disclosed herein include an apoA-IV protein comprising an amino acid sequence which is 95%, 96%, 97%, 98%, or 99% identical to a sequence as set forth in SEQ ID NOs: 1, 3, 4 or 6-51, or a biologically active fragment thereof.

These and other features and advantages of these and other various embodiments according to the present disclosure will become more apparent in view of the drawings, detailed description, and claims provided herein.

BRIEF DESCRIPTION OF THE DRAWINGS

The following detailed description of the embodiments of the present disclosure can be better understood when read in conjunction with the following drawings, where like structure is indicated with like reference numerals, and in which:

FIG. 15 is a protein with the amino acid sequence of full length wild type human apolipoprotein A-IV (SEQ ID NO. 1).

FIG. 16 is a protein with the amino acid sequence of full length wild type mouse apolipoprotein A-IV (SEQ ID NO. 2).

FIG. 17 is a protein with the amino acid sequence of full length wild type human apolipoprotein A-IV with the addition of glycine at the N-terminus (SEQ ID NO. 3).

FIG. 18 is a protein with the amino acid sequence of human apolipoprotein A-IV showing polymorphic substitutions T347S, Q360H, and/or E165K and the optional addition of glycine, alanine or valine to the N-terminus (SEQ ID NO. 4).

FIG. 19 is a polynucleotide (SEQ ID NO. 5) encoding full length wild type human apolipoproteom A-IV.

Figure 1:
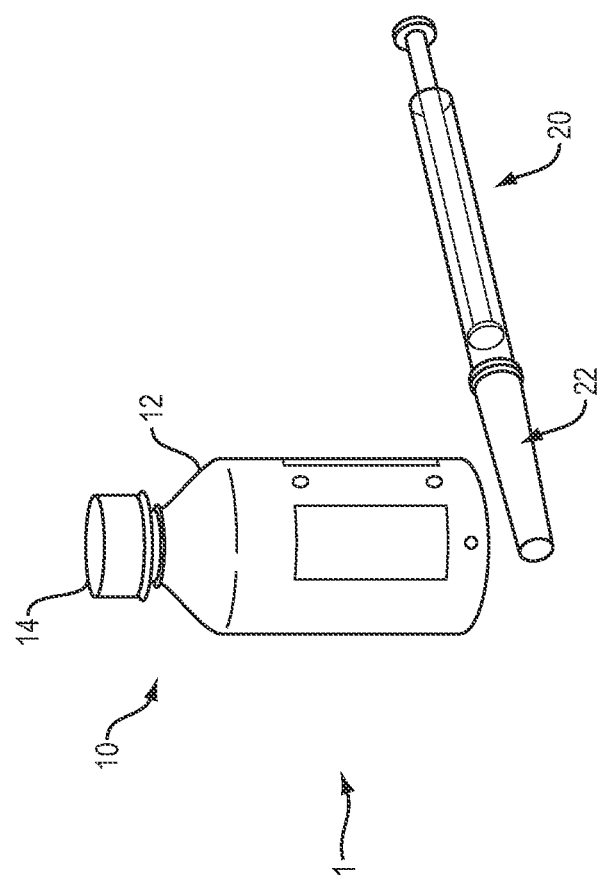
FIG. 1 is a side perspective view of a device having a reservoir of a pharmaceutical composition and a syringe according to an embodiment of the present disclosure.

Skilled artisans appreciate that elements in the figures are illustrated for simplicity and clarity and are not necessarily drawn to scale. For example, the dimensions of some of the elements in the figures may be exaggerated relative to other elements, as well as conventional parts removed, to help to improve understanding of the various embodiments of the present disclosure.

DETAILED DESCRIPTION

The following terms are used in the present application:

As used herein, the term "hyperglycemic disorders" or "disorder associated with hyperglycemia" refers to a disorder in which a subject's blood sugar is elevated. The resulting increase in blood glucose may raise levels outside the normal range and cause adverse health effects for the subject. Examples of hyperglycemic disorders include, but are not limited to, diseases associated with insulin resistance (including, but not limited to, prediabetes, metabolic syndrome, Type A Insulin Resistance Syndrome, hyperglycemia or insulin resistance associated with polycystic ovarian disease, gestational diabetes), and hyperglycemia associated with endocrine abnormalities (including but not limited to Cushing's Disease, glucagon secreting tumors, and Acromegaly). In one embodiment, a hyperglycemic disorder does not include type II diabetes.

As used herein, the term "disorder associated with insulin resistance" refers to a condition where insulin becomes less effective at lowering blood sugar. Examples include, but are not limited to, prediabetes, metabolic syndrome, Type A Insulin Resistance Syndrome, hyperglycemia or insulin resistance associated with polycystic ovarian disease, gestational diabetes.

As used herein, the term "endocrine disorder associated with hyperglycemia" refers to disorders of the endocrine system characterized by high blood sugar. Examples of endocrine disorders associated with hyperglycemia include, but are not limited to Cushing's Disease, glucagon secreting tumors, and Acromegaly.

As used herein, the term "prediabetes" means a condition characterized by one or more of the following factors: the presence of anti-islets of Langerhans cells immunological markers, an impairment in the number of islets of Langerhans cells, suppression of the early peak of insulin secretion, glucose intolerance, an impairment tin fasting glycaemia and/or any diabetic risk factor. Prediabetes is characterized either by impaired glucose tolerance or impaired fasting glucose and often described as the "gray area" between the normal level and diabetic levels of blood sugar. Prediabetes often precedes type two diabetes.

As used herein, the term "effective amount" describes the amount necessary or sufficient to realize a desired biologic effect. The effective amount for any particular application may vary depending on a variety of factors, including but not limited to the particular composition being administered, the size of the subject, and/or the severity of the disease and/or condition being treated. In one embodiment, an "effective amount" is a dose of about 0.25 to 10 μg/g of an apolipoprotein A-IV or biologically active analogue thereof. Alternatively, an "effective amount of an apoA-IV or a biologically active analogue thereof is about 1 to 10 μg/g, about 0.25 to 2 μg/g, about 1 μg/g, or 0.1 mg/kg to 25 mg/kg. In another embodiment, the effective amount is a fixed dose of about 1 to 1000 mg. In a further embodiment, the effective amount is a fixed dose of about 1 to 10 mg. An apoA-IV or a biologically active analogue is administered one time daily. Alternatively, an apoA-IV or a biologically active analogue thereof is administered about 2 times per day. In yet another alternative, an apoA-IV or a biologically active analogue thereof is administered more than twice a day, for example, three times per day. In yet another alternative, apoA-IV is administered once every second, third, fourth, fifth or sixth day, or once weekly.

As used herein, the term "desired biologic effect" describes reducing the effects of, counteracting, and/or eliminating a disease or condition. For example, in the context of hyperglycemic disorders, desired biologic effects include, but are not limited to lowering blood glucose, improving glucose tolerance, substantially restoring glucose tolerance to a normal level, improving insulin secretion, and/or substantially restoring insulin secretion to a normal level.

As used herein, the term "normal level" describes a level that is substantially the same as the level in a subject who is not in need of treatment. For example, in the context of treating a hyperglycemic disorder, a normal level of blood glucose is from about 70 mg/dL to about 130 mg/dL before meals and less than about 180 mg/dL about one to two hours after meals, or from about 70 mg/dL to about 100 mg/dL before meals and less than about 140 mg/dL about one to two hours after meals. In another example in the context of treating a hyperglycemic disorder, a normal level of glucose tolerance describes the ability of the subject to metabolize carbohydrates such that the level of blood glucose is from about 70 mg/dL to about 130 mg/dL before meals and less than about 180 mg/dL about one to two hours after meals, or from about 70 mg/dL to about 100 mg/dL before meals and less than about 140 mg/dL about one to two hours after meals. In still another example in the context of treating a hyperglycemic disorder, the normal level of insulin secretion is the amount required to maintain a normal level of glucose tolerance, wherein the level of insulin secretion is greater than about 1 ng/mL about fifteen hours after meals. In a further embodiment, a normal level of blood glucose is from about 70 mg/dl to 100 mg/dl for a morning fasting blood sugar test.

In the context of blood glucose level, the term "restore" describes changing the blood glucose level of a subject to a normal level. Similarly, in the context of glucose tolerance, the term "restore" describes changing the glucose tolerance of a subject to a normal level. Also, in the context of insulin secretion, "restore" describes changing the insulin secretion of a subject to a normal level or to one sufficient to lower blood glucose.

In the context of apolipoprotein A-IV, the term "biologically active fragment" describes a fragment of apolipoprotein A-IV which is capable of realizing a desired biologic effect in a subject with a hyperglycemic disorder, e.g., restore glucose tolerance. The term "biologically active analogue" describes an analogue of an apolipoprotein A-IV which is capable of realizing a desired biologic effect in a subject with a hyperglycemic disorder, e.g., restore glucose tolerance. In one example, a desired biological effect is to restore glucose tolerance in apoA-IV knockout mice as described in Example 2. Another example of a desired biological effect is to cause a statistically significant lowering of abnormal glucose levels in an animal model of type 2 diabetes (T2DM), such as the mouse model described in Example 7.

The phrase "percent identical" or "percent identity" refers to the similarity (e.g., 95%, 96%, 97%, 98%, or 99%) between at least two different sequences. This percent identity can be determined by standard alignment algorithms, for example, the Basic Local Alignment Search Tool (BLAST) described by Altshul et al. ((1990) J. Mol. Biol. 215:403-10); the algorithm of Needleman et al. ((1970) J. Mol. Biol. 48:444-53); or the algorithm of Meyers et al. ((1988) Comput. Appl. Biosci. 4:11-17). A set of parameters may be, for example, the Blosum 62 scoring matrix with a gap penalty of 12, a gap extend penalty of 4, and a frameshift gap penalty of 5. The percent identity between two amino acid or nucleotide sequences can also be determined using the algorithm of Meyers and Miller ((1989) CABIOS 4:11-17), which has been incorporated into the ALIGN program (version 2.0), using a PAM120 weight residue table, a gap length penalty of 12, and a gap penalty of 4.

The term "recombinant protein" refers to a protein molecule that is expressed from recombinant DNA. For example, a recombinant ApoA-IV protein is one that is expressed in a recombinant host cell.

As used herein, the term "obese" describes a condition in which a subject is well above a normal weight. In one specific example, the term obese describes a condition in which a subject is more than about 20% over their ideal weight and/or has a body mass index of about thirty or greater than about thirty. In one embodiment, the subject being treated is obese; in another embodiment, the subject being treated is not obese; and in yet another embodiment, the subject being treated has a normal body weight.

Embodiments of the present disclosure relate to methods for treating a hyperglycemic disorder in a subject in need thereof and pharmaceutical compositions for the treatment of hyperglycemic disorder. In one embodiment, a method of treating diabetes is disclosed. In one particular embodiment, a method of treating a hyperglycemic disorder in a subject in need thereof is disclosed, wherein the method comprises administering an effective amount of an apoA-IV or a biologically active analogue thereof to the subject.

In one embodiment, the method of treating a hyperglycemic disorder results in a lower blood glucose level of a subject. In one particular embodiment, the method is effective to lower blood glucose level of a subject by about 20 to 60%. In a further embodiment, the method is effective to lower the blood glucose level of a subject by about 70%. In a further embodiment, the method is effective to lower the blood glucose level of a subject by about 40%. In still a further embodiment, the method is effective to substantially restore blood glucose level to a lower than previous levels or to normal level.

In one embodiment, the method of treating a hyperglycemic disorder results in a lower blood glucose level of a subject. In one particular embodiment, the method is effective to lower blood glucose level of a subject by about 1 mg/dl, 2 mg/dl, 3 mg/dl, 4 mg/dl, 5 mg/dl, 6 mg/dl, 7 mg/dl, 8 mg/dl, 9 mg/dl, 10 mg/dl, 11 mg/dl, 12 mg/dl, 13 mg/dl, 14 mg/dl, 15 mg/dl, 16 mg/dl, 17 mg/dl, 18 mg/dl, 19 mg/dl, 20 mg/dl, 40 mg/dl, 60 mg/dl, 80 mg/dl, 100 mg/dl, 120 mg/dl, 140 mg/dl, 160 mg/dl, 180 mg/dl, 200 mg/dl, 220 mg/dl, or 240 mg/dl, from a baseline level over the course of the dosing interval.

In another embodiment, the method of treating a hyperglycemia disorder is effective to substantially restore glucose tolerance of a subject to a normal level. In one particular embodiment, the method is effective to substantially restore glucose tolerance of a subject to a normal level within about two hours after administration of a dose of an apoA-IV or a biologically active analogue thereof. In another embodiment, the method is effective to substantially restore glucose tolerance of a subject to a normal level within about three hours or within about four hours after administration of a dose of an apoA-IV or a biologically active analogue thereof. In another embodiment, the glucose tolerance of a subject is substantially restored to a normal level for about eight to twelve hours.

In yet another embodiment, the treatment is effective to substantially restore insulin secretion to a normal level. In one particular embodiment, the treatment is effective to substantially restore insulin secretion to a normal level within about two hours after the administration of a dose of an apoA-IV or a biologically active analogue thereof. In another embodiment, insulin secretion is substantially restored to a normal level for about eight to twelve hours. In still another embodiment, the treatment is effective to lower the level of C-reactive protein.

As described above, examples of hyperglycemic disorders include, but are not limited to, disorders associated with insulin resistance. Examples of insulin resistant disorders include, but are not limited to, prediabetes, metabolic syndrome, polycystic ovary disease, type A syndrome and other insulin resistant genetic disorders, and gestational diabetes.

In one embodiment, the invention provides a method of treating prediabetes in a subject by administering apoA-IV. A person having prediabetes has blood sugar levels that are higher than normal, but not yet high enough to be classified as type 2 diabetes. Prediabetes can be characterized through a number of tests. For example, the glycated hemoglobin (A1C) test may be used to diagnose prediabetes. The A1C blood test indicates the average blood sugar level for the past two to three months of the subject. An A1C level between 6 and 6.5 percent is considered prediabetic, whereas a level of 6.5 percent or higher on two separate tests indicates diabetes.

Other tests for prediabetes include the fasting blood sugar test and the glucose tolerance test. Impaired fasting glucose is determined by measuring glucose levels after a fast of at least eight hours or overnight. Impaired glucose fasting indicating prediabetes is defined as 100 to 125 mg/dL (5.6 to 6.9 mmol/L), whereas a blood sugar level lower than 100 milligrams per deciliter (mg/dL)—5.6 millimoles per liter (mmol/L)—is normal. A blood sugar level of 126 mg/dL (7.0 mmol/L) or higher may indicate diabetes mellitus.

Alternatively, prediabetes may be characterized by the impaired glucose tolerance test where glucose levels are measured following the consumption of a sugary solution (generally two hours following ingestion). For the impaired glucose tolerance test, a blood sugar level less than 140 mg/dL (7.8 mmol/L) is normal, whereas a blood sugar level from 140 to 199 mg/dL (7.8 to 11.0 mmol/L) is considered prediabetic and often referred to as impaired glucose tolerance (IGT). A blood sugar level of 200 mg/dL (11.1 mmol/L) or higher may indicate diabetes mellitus. As such, the invention provides a means for treating prediabetes by administration of apoA-IV.

In one embodiment, the invention provides a method of treating metabolic syndrome in a subject by administering apoA-IV. Metabolic Syndrome (also referred to as Syndrome X or insulin resistance syndrome), is the name for a group of risk factors that occur together and increase a person's risk for coronary artery disease, stroke, and type 2 diabetes. While metabolic syndrome is becoming more and more common in the United States, it is unknown whether the syndrome is due to one single cause, but all of the risks for the syndrome are related to obesity. The two most important risk factors for metabolic syndrome are 1. extra weight around the middle and upper parts of the body (central obesity) of the body and 2. insulin resistance, in which the body cannot use insulin effectively. According to the American Heart Association and the National Heart, Lung, and Blood Institute, metabolic syndrome is present if you have three or more of the following signs: 1. blood pressure equal to or higher than 130/85 mmH; 2. a fasting blood sugar (glucose) equal to or higher than 100 mg/d; 3. a large waist circumference (length around the waist), defined as 40 inches or more for men and 35 inches or more for women; 4. low HDL cholesterol levels, defined as under 40 mg/dl for men and under 50 mg/dl for women; and 5. triglycerides equal to or higher than 150 mg/dL. As such, the invention provides a means for treating metabolic syndrome by administration of apoA-IV.

In one embodiment, the invention provides a method of treating insulin resistance and hyperglycemia in a subject having polycystic ovary disease by administering apoA-IV. Polycystic ovary disease (also referred to as Stein-Leventhal syndrome or polyfollicular ovarian disease) is a condition in which a woman has an imbalance of a female sex hormones, and may lead to menstrual cycle changes, cysts in the ovaries, fertility issues, and other health changes. While the causes of polycystic ovary disease are not fully understood, one of the major biochemical features of polycystic ovary syndrome is insulin resistance accompanied by compensatory hyperinsulinemia (elevated fasting blood insulin levels). Indeed, type II diabetes is often a long-term complication associated with the disease. Thus, the invention provides a means for treating insulin resistance and hyperglycemia in a subject having polycystic ovary disease by administration of apoA-IV.

In a further embodiment, the methods and compositions of the invention may also be used to treat genetic disorders associated with extreme insulin resistance, including, but not limited to, Donohue syndrome, Rabson-Mendenhall syndrome, and type A insulin resistance. Donohue syndrome is characterized by intrauterine growth restriction, failure to thrive after birth, loss of glucose homeostasis and hyperinsulinemia, among other conditions. Patients diagnosed with Donohue syndrome have a shortened life expectancy, and generally do not live more than a year. Rabson-Mendenhall syndrome is characterized by growth retardation and hyperinsulinemia, among other symptoms. Type A insulin resistance may present with hirsutism, reduced subcutaneous fat, diabetes mellitus, acanthosis nigricans, and hyperinsulinemia, as well as amenorrhea and polycystic ovaries in females. Hyperinsulinemia, a biological marker for insulin resistance, is often associated with glucose tolerance defects over the course of the disease, and diabetes progressively sets in. As such, apoA-IV may be used to treat patients having inherited diseases associated with extreme insulin resistance, such as type A insulin resistance syndrome.

In a further embodiment, the methods and compositions of the invention may also be used to treat gestational diabetes. Gestational diabetes is characterized as high blood sugar levels (see tests described above for prediabetes which can be used to determine gestational diabetes as well). While gestational diabetes generally disappears upon the birth of the child, sugar levels must be maintained during pregnancy for the health of the mother and baby. Moreover, gestational diabetes is often a precursor to prediabetes. Thus, apoA-IV may be used to lower sugar levels in subjects having gestational diabetes.

As described above, examples of hyperglycemic disorders include, but are not limited to, endocrine disorders associated hyperglycemia. Examples of endocrine disorders associated hyperglycemia include, but are not limited to, Cushing's Disease, increased glucagon secretion, and Acromegaly In one embodiment, the methods and compositions of the invention may be used to treat Cushing's disease. Cushing's disease is characterized by an excess cortisol production by adrenal glands. Symptoms include high blood sugar levels along with high blood pressure, weariness, obesity in the upper part of body and slenderness in legs and arms.

In another embodiment, the methods and compositions of the invention may be used to treat glucagon secreting tumors. A glucagon secreting tumor is also called a glucagonoma, and is a rare tumor of the alpha cells of the pancreas that results in up to a 1000-fold overproduction of the hormone glucagon. The primary physiological effect of glucagonoma is an overproduction of the peptide hormone glucagon, which enhances blood glucose levels through the activation of anabolic and catabolic processes including gluconeogenesis and lipolysis, respectively.

In yet another embodiment, the methods and compositions of the invention may be used to treat acromegaly. Acromegaly is a metabolic disorder caused by a pituitary gland tumor, which results in an overproduction of human growth hormone.

In one embodiment, the invention includes a method of first selecting a subject having one of the aforementioned disorders and administering ApoA-IV, or a biologically active fragment thereof, for the treatment of said disorder.

In one embodiment, an apoA-IV or a biologically active analogue thereof is administered systemically. Systemic administration of the apoA-IV or the analogue thereof is selected from the group consisting of oral, subcutaneous, intravenous, intramuscular, and intraperitoneal administration.

In another embodiment, a pharmaceutical composition is disclosed. In one particular embodiment, the pharmaceutical composition comprises an apoA-IV or a biologically active analogue thereof. In another embodiment, the apoA-IV or analogue thereof is formulated for administration to a subject for the treatment of hyperglycemic disorders. In this particular embodiment, a method for treating hyperglycemic disorders in a subject in need thereof is also provided, wherein the method comprises administering an effective amount of the pharmaceutical composition to the subject.

An "apolipoprotein A-IV" (also referred to herein as "apoA-IV") refers to mammalian apoA-IV and includes full-length apoA-IV and biologically active fragments of apoA-IV. The full-length human apoA-IV is a 376 amino acid protein (SEQ ID NO: 1), the amino acid sequence of which is shown in FIG. 15; the amino acid sequence of full length mouse apoA-IV (SEQ ID NO: 2) is shown in FIG. 16. Also encompassed by the term "apolipoprotein A-IV" is the known analogue in which a glycine is added to N-terminus of the apolipoprotein A-IV of the full length human sequence (SEQ ID NO. 3, as shown in FIG. 17), and analogues thereof having conservative substitutions for the N-terminal glycine (such as alanine and valine). An "apolipoprotein A-IV" also includes polymorphic forms thereof, including the T347S, Q360H, or E165K substitutions to the human sequence represented by SEQ ID NO. 1 or the corresponding positions of SEQ ID NO. 3. As such, "apolipoprotein A-IV" includes the protein of SEQ ID NO. 4, shown in FIG. 18. Variant versions of apoA-IV are also included in the methods and compositions of the invention, and include variants containing the following missense mutations: P393H, Q385K, Q381K, Q380H, Q377P, T367S, S353A, N352Y, V336M, D335H, G311R, V307L, R305C, R304Q, E291G, V274M, V274A, R264Q, A260T, E250K, N235S, Q231K, R220C, Q214H, E207K, T202M, R200C, D191N, D184N, P181L, A172T, R169W, A161S, R154W, T148M, S147N, A139E, N127K, S95L, R90C, T85A, Q77H, G74S, V13M, or V6M (see SEQ ID Nos: 6-50). SEQ ID NO: 51 represents the amino acid sequence of ApoA-IV having the signal sequence. ApoA-IV proteins having 95%, 96%, 97%, 98%, or 99% identity the amino acid sequences described in SEQ ID NOs: 1, 3, 4, and 6-51, or biologically active fragments thereof, are also contemplated in the methods of the invention.

A biologically active analogue of apolipoprotein A-IV has at least 90, 95, 96, 97, 98 or 99% identity to an apolipoprotein A-IV. As described in the previous paragraph, an apolipoprotein A-IV includes full length mammalian apolipoprotein A-IV (e.g., human or mammalian), polymorphic forms thereof, the protein of SEQ ID NOS. 3 and 4, and biologically active fragments of any of the foregoing. Amino acid variations in the biologically active analogues preferably have conservative substitutions relative to the wild type sequences. A "conservative substitution" is the replacement of an amino acid with another amino acid that has the same net electronic charge and approximately the same size and shape. Amino acid residues with aliphatic or substituted aliphatic amino acid side chains have approximately the same size when the total number of carbon and heteroatoms in their side chains differs by no more than about four. They have approximately the same shape when the number of branches in their side chains differs by no more than one. Amino acid residues with phenyl or substituted phenyl groups in their side chains are considered to have about the same size and shape. Listed below are five groups of amino acids. Replacing an amino acid residue with another amino acid residue from the same group results in a conservative substitution:

Group I: glycine, alanine, valine, leucine, isoleucine, serine, threonine, cysteine, and non-naturally occurring amino acids with C1-C4 aliphatic or C1-C4 hydroxyl substituted aliphatic side chains (straight chained or monobranched).

Group II: glutamic acid, aspartic acid and non-naturally occurring amino acids with carboxylic acid substituted C1-C4 aliphatic side chains (unbranched or one branch point).

Group III: lysine, ornithine, arginine and non-naturally occurring amino acids with amine or guanidino substituted C1-C4 aliphatic side chains (unbranched or one branch point).

Group IV: glutamine, asparagine and non-naturally occurring amino acids with amide substituted C1-C4 aliphatic side chains (unbranched or one branch point).

Group V: phenylalanine, phenylglycine, tyrosine and tryptophan.

Apolipoprotein A-IV or a biologically active analogue thereof can be glycosylated or unglycosylated. The preparation of recombinant unglycosylated human and mouse apolipoprotein A-IV is described in Example 11. The polynucleotide sequence of full length wild type human apolipoprotein (SEQ ID NO. 1) is shown as SEQ ID NO. 5 in FIG. 19. Apolipoprotein A-IV used in examples 1-11 is unglycosylated. ApoA-IV may be prepared according to a method known in the molecular biology field. For example, apoA-IV may be prepared via traditional molecular cloning techniques.

In one embodiment, a bacterial host may be used to produce non-glycosylated apoA-IV. Examples of bacterial hosts include, but are not limited to, *E. coli* BL-21, BL-21 (DE3), BL21-AI™, BL21(DE3)pLysS, BL21(DE3)pLysE, BL21 Star™ (DE3), and BL21 Star™ (DE3)pLysS, (Invitrogen). *Corynebacterium* may also be used as a host cell for expressing apoA-IV. Prior to transformation into the bacterial host, the DNA segment encoding ApoA-IV or its analogue may be incorporated in any of suitable expression vectors for transformation into the bacterial host. Suitable expression vectors include plasmid vectors, cosmid vectors, and phage vectors variously known to those of skill in the art, for example, as described in Sambrook, et al., Molecular Cloning Manual, 2d Edition, 1989. Examples of the expression vector include pET Vectors (Invitrogen), pDEST vectors (Invitrogen), pRSET vectors (Invitrogen), and pJexpress Vector (DNA2.0 Inc.). In one embodiment, E. Coli BL-21 (DE3) is transformed with pET30 expression vector which contains the gene encoding the ApoA-IV.

In addition to prokaryotes, eukaryotic microbes such as filamentous fungi or yeast are suitable cloning or expression hosts for apoA-IV-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of apoA-IV are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

Another suitable host cell for production of apoA-IV protein is a vertebrate cell. Examples of useful mammalian host cell lines are monkey kidney CV1 line transformed by SV40 (COS-7, ATCC CRL 1651); human embryonic kidney line (e.g., 293 or 293 cells subcloned for growth in suspension culture, Graham et al., J. Gen Virol. 36:59 (1977)); baby hamster kidney cells (BHK, e.g., ATCC CCL 10); Chinese hamster ovary cells/-DHFR(CHO, Urlaub et al., Proc. Natl. Acad. Sci. USA 77:4216 (1980)), including, but not limited to CHO K1, CHO pro3-, CHO DG44, CHO DUXB11, Lec13, B-Ly1, and CHO DP12 cells, preferably a CHO DUX (DHFR-) or subclone thereof (herein called "CHO DUX"); C127 cells, mouse L cells; Ltk.sup.-cells; mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse myeloma cells; NS0; hybridoma cells such as mouse hybridoma cells; COS cells; mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2).

Host cells are transformed with expression or cloning vectors for production of the apoA-IV protein, and cultured in conventional nutrient media modified as appropriate for inducing promoters, selecting transformants, or amplifying the genes encoding the desired sequences.

Apolipoprotein A-IV knockout mice used in the examples were generated according to procedures disclosed in J Lipid Res. 1997 September; 38(9):1782-94, the entire teachings of which are incorporated herein by reference.

In one particular embodiment, the pharmaceutical composition may further comprise a pharmaceutically acceptable carrier. Pharmaceutically acceptable carriers include a wide range of known diluents (i.e., solvents), fillers, extending agents, binders, suspending agents, disintegrates, surfactants, lubricants, excipients, wetting agents and the like commonly used in this field. The pharmaceutical composition is preferably aqueous, i.e., is a liquid formulation, and preferably comprises pyrogen free water. These carriers may be used singly or in combination according to the form of the pharmaceutical preparation. The resulting preparation may incorporate, if necessary, one or more solubilizing agent, buffers, preservatives, colorants, perfumes, flavorings and the like that are widely used in the field of pharmaceutical preparation.

The apolipoprotein A-IV or biologically active analogue thereof may be formulated into a dosage form selected from the group consisting of tablets, capsules, granules, pills, injections, solutions, emulsions, suspensions, and syrups. The form and administration route for the pharmaceutical composition are not limited and can be suitably selected. For example, tablets, capsules, granules, pills, syrups, solutions, emulsions, and suspensions may be administered orally. Additionally, injections (e.g. subcutaneous, intravenous, intramuscular, and intraperitoneal) may be administered intravenously either singly or in combination with a conventional replenisher containing glucose, amino acid and/or the like, or may be singly administered intramuscularly, intracutaneously, subcutaneously and/or intraperitoneally.

The pharmaceutical composition of the invention for treating hyperglycemia may be prepared according to a method known in the pharmaceutical field of this kind using a pharmaceutically acceptable carrier. For example, oral forms such as tablets, capsules, granules, pills and the like are prepared according to known methods using excipients such as saccharose, lactose, glucose, starch, mannitol and the like; binders such as syrup, gum arabic, sorbitol, tragacanth, methylcellulose, polyvinylpyrrolidone and the like; disintegrates such as starch, carboxymethylcellulose or the calcium salt thereof, microcrystalline cellulose, polyethylene glycol and the like; lubricants such as talc, magnesium stearate, calcium stearate, silica and the like; and wetting agents such as sodium laurate, glycerol and the like.

Injections, solutions, emulsions, suspensions, syrups and the like may be prepared according to a known method suitably using solvents for dissolving the active ingredient, such as ethyl alcohol, isopropyl alcohol, propylene glycol, 1,3-butylene glycol, polyethylene glycol, sesame oil and the like; surfactants such as sorbitan fatty acid ester, polyoxyethylenesorbitan fatty acid ester, polyoxyethylene fatty acid ester, polyoxyethylene of hydrogenated castor oil, lecithin and the like; suspending agents such as cellulose derivatives including carboxymethylcellulose sodium, methylcellulose and the like, natural gums including tragacanth, gum arabic and the like; and preservatives such as parahydroxybenzoic acid esters, benzalkonium chloride, sorbic acid salts and the like.

The proportion of the active ingredient to be contained in the pharmaceutical composition of the invention for treating a hyperglycemic disorder can be suitably selected from a wide range.

Also included in the methods of the invention are combination therapies for treating hyperglycemic disorders. Examples of additional therapeutic agents that may be used in combination with apolipoprotein A-IV include, but are not limited to, sulfonylureas, meglitinides, biguanides, thiazolidinediones, alpha-glucosidase inhibitors, DPP-4 inhibitors, incretin mimetics, and insulin. An additional therapeutic agent may be administered prior to, concurrently with, or subsequent to administration of apoA-IV to the subject in need thereof.

The effective amount or apoA-IV administered to a subject for the treatment of a disorder associated with hyperglycemia may, for example, be a weight-based dose (e.g., mg/kg) or, in another example, be a fixed dose (non-weight dependent). In one embodiment, about 1 to 10 mg/kg, about 0.25 to 2 mg/kg, about 1 mg/kg, or 0.1 mg/kg to 25 mg/kg of apoA-IV is administered to a subject in need thereof. In another embodiment, the effective amount of apoA-IV administered to a subject in need thereof is a fixed dose of about 1 to 1000 mg. In a further embodiment, the effective amount is a fixed dose of apoA-IV administered to a subject in need thereof, is about 1 mg, 2 mg, 3 mg, 4 mg, 5 mg, 6 mg, 7 mg, 8 mg, 9 mg, 10 mg, 11, mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 40 mg, 50 mg, 60 mg, 70 mg, 80 mg, 90 mg, 100 mg, 120 mg, 140 mg, 160 mg, 180 mg, 200 mg, 250 mg, 300 mg, 350 mg, 400 mg, 450 mg, 500 mg, 550 mg 600 mg, 650 mg, 700 mg, 750 mg, 800 mg, 850 mg, 900 mg, 950 mg, or 1000 mg.

In one particular embodiment, the subject in need of treatment of a hyperglycemic disorder is a mammal. The mammal may be selected from the group consisting of humans, non-human primates, canines, felines, murines, bovines, equines, porcines, and lagomorphs. In one specific embodiment, the mammal is human. In another embodiment, apoA-IV or a biologically active analogue thereof may be administered to a subject for the treatment of a hyperglycemic disorder wherein the subject is obese. Alternatively, apoA-IV may be administered to a subject for the treatment of a hyperglycemic disorder wherein the subject is not obese.

Referring to FIG. 1, in yet another embodiment, a device 1 is disclosed. In one embodiment, the device 1 comprises a reservoir 10 of the pharmaceutical composition previously discussed above. In a further embodiment, the reservoir 10 comprises a vial 12. The vial 12 may be formed of any material that does not inhibit the function of the pharmaceutical composition. For example, the vial 12 may comprise glass and/or plastic. Additionally, the vial 12 may comprise a pierceable septum 14 through which the pharmaceutical composition may be removed. In use, the septum 14 of the vial is pierced by the needle 22 of a syringe 20, the pharmaceutical composition is removed by the syringe 20 from the vial 12, and the pharmaceutical composition is administered via injection to a subject in need.

EXAMPLES

The following non-limiting examples illustrate the methods of the present disclosure.

Example 1: Glucose Intolerance of ApoA-IV Knockout Mice

Experimental Protocol.

Male apoA-IV knockout ("hereinafter "KO") mice were obtained. Wild-type (hereinafter "WT") mice served as controls. ApoA-IV KO and WT mice were obtained from a colony kept at the University of Cincinnati (Cincinnati, Ohio). ApoA-IV KO and WT mice were fed a chow diet. Prior to performing the glucose tolerance tests, ApoA-IV KO mice and WT mice were fasted for five hours. In the glucose tolerance tests, the apoA-IV KO mice and WT mice were injected intraperitoneally with a dose of about 2 mg/g body weight of glucose and plasma glucose was measured at about 0, 15, 30, 60, and 120 minutes following the injection of glucose. The glucose tolerance tests were performed twice, once at three months of age and again at sixteen months of age.

Experimental Results.

Figure 2:
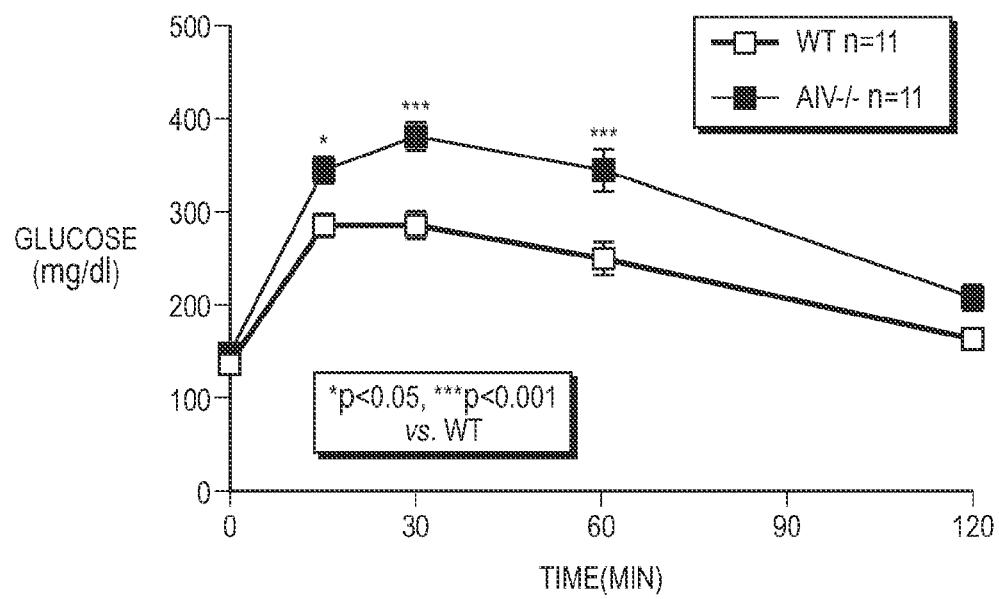
FIG. 2 is a graph of plasma glucose (mg/dL) in male apolipoprotein A-IV knockout and wild-type mice with respect to time (min) for an intraperitoneal glucose tolerance test.
Figure 3:
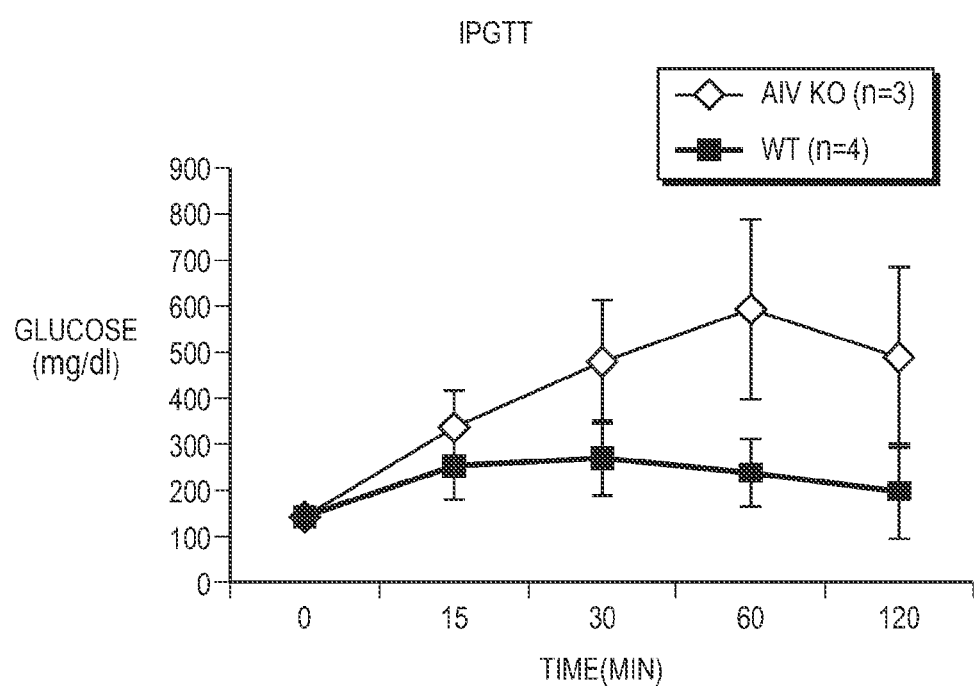
FIG. 3 is a graph of plasma glucose (mg/dL) with respect to time (min) for an intraperitoneal glucose tolerance test in apolipoprotein A-IV wild-type and knockout animals at 16 months of age.

As shown in FIG. 2, apoA-IV KO mice were glucose intolerant relative to the WT mice. Specifically, FIG. 2 shows that plasma glucose levels in WT mice were lower than plasma glucose levels in apoA-IV KO mice for two hours following intraperitoneal injection with glucose. While not being bound by the theory, the implication of these studies was that apoA-IV is necessary for normal glucose homeostasis (at least in males). Moreover, as shown in FIG. 3, apoA-IV KO mice demonstrated an increased glucose intolerance when tested at sixteen months of age. Specifically, FIG. 3 shows that plasma glucose levels in apoA-IV KO mice tested at sixteen months of age were higher than the plasma glucose levels in apoA-IV KO tested at three months of age. While not being bound by the theory, the implication of these studies was that glucose tolerance of apoA-IV KO mice worsens with age.

Experiment with Female Wild Type and ApoA-IV Knockout Mice.

Figure 11:
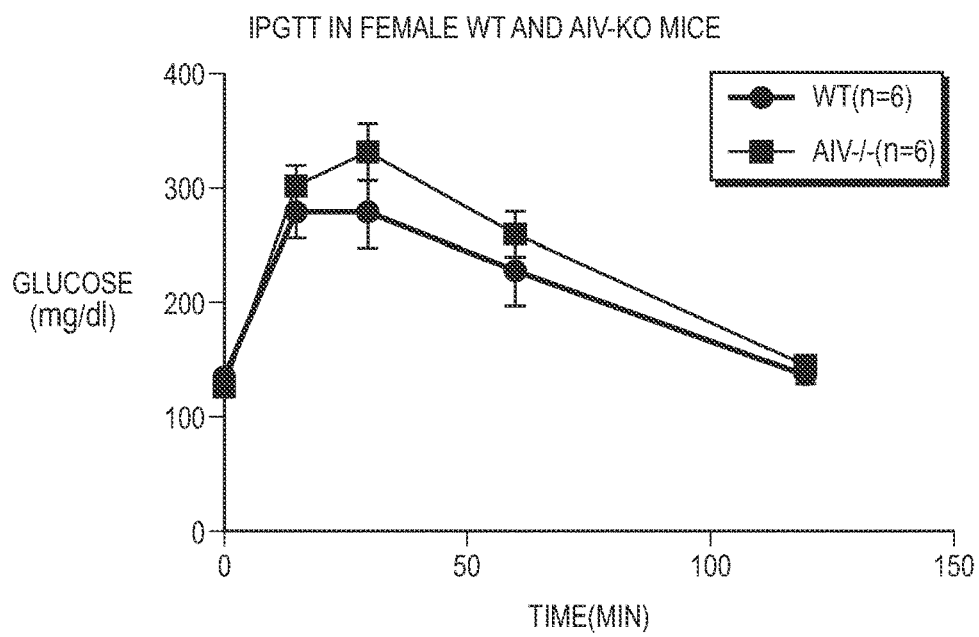
FIG. 11 is a graph of plasma glucose (mg/dL) in female apolipoprotein A-IV knockout and wild-type mice with respect to time (min) during an intraperitoneal glucose tolerance test (IPGTT).

Female ApoA-IV wildtype and knockout mice were subjected to the same inraperitoneal glucose itolerance test as was used for the male apoA-IV KO and WT mice, as described earlier in this Example 1. The results are shown in FIG. 11. Female apoA-IV$^{-/-}$ mice, when challenged intraperitoneally with glucose, have increased plasma glucose levels compared with female WT animals, but there is no statistical significant difference. On the other hand, the males have a significant difference between WT and KO animals.

Example 2: Restoration of Glucose Tolerance in ApoA-IV Knockout Mice

Experimental Protocol.

Upon demonstrating that apoA-IV KO mice are glucose intolerant, a series of extensive studies were performed to determine whether administration of apoA-IV to apoA-IV KO mice would restore glucose tolerance to a normal level. Specifically, a series of studies were performed to determine not only the amount of apoA-IV to be administered but also the optimal time in which to administer apoA-IV prior to conducting glucose tolerance tests.

ApoA-IV male KO mice were injected intraperitoneally with doses of about 0.25, 0.5, 1, and 2 µg/g by weight of apoA-IV. ApoA-IV KO mice were also injected intraperitoneally with saline solution to serve as a control. Following injection with mouse apoA-IV or saline solution, glucose tolerance tests were conducted at three months of age as previously discussed. Specifically, glucose tolerance tests were conducted about two hours following injection with apoA-IV or saline solution. Experimental results indicated that the optimal time to restore glucose tolerance in apoA-IV KO mice was to administer apoA-IV about two hours prior to conducting glucose tolerance tests.

Experimental Results.

Figure 4:
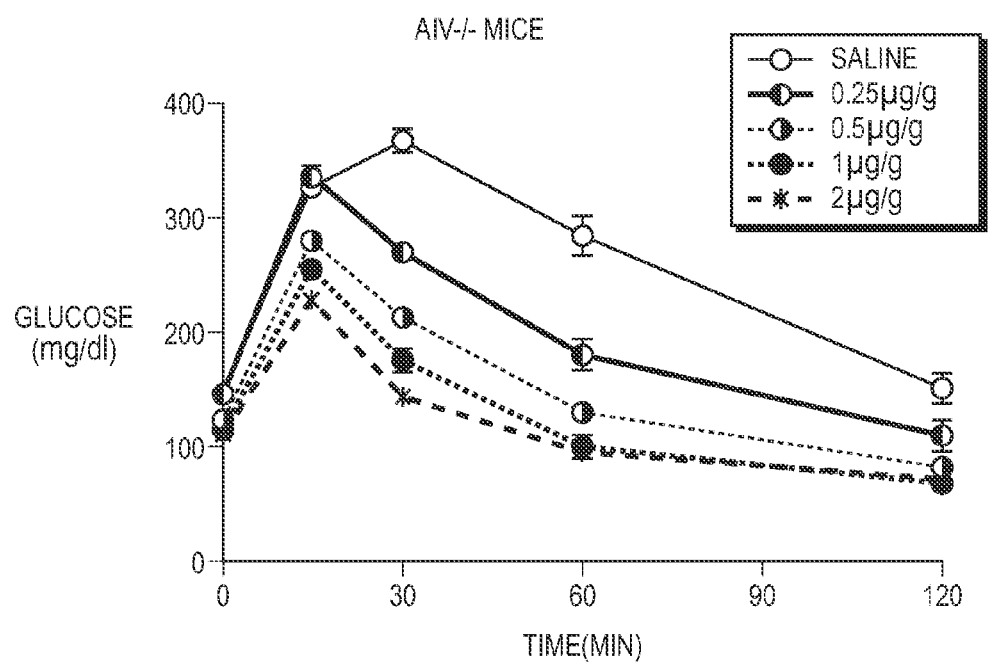
FIG. 4 is a graph of plasma glucose (mg/dL) with respect to time (min) in male apolipoprotein A-IV knockout mice following the intraperitoneal administration of recombinant apolipoprotein A-IV (µg/g) or saline solution for an intraperitoneal glucose tolerance test.

As shown in FIG. 4, the administration of apoA-IV to apoA-IV KO mice restored glucose tolerance to a normal level. Specifically, FIG. 4 shows that plasma glucose levels in apoA-IV KO mice injected with apoA-IV were lower than plasma glucose levels in apoA-IV KO mice injected with saline solution. Moreover, as shown in FIG. 4, plasma glucose levels in apoA-IV KO mice injected with apoA-IV were the lowest in the apoA-IV KO mice injected with the highest dosage of apoA-IV; similarly, plasma glucose levels in apoA-IV KO mice injected with apoA-IV were the highest in the apoA-IV KO mice injected with the lowest dosage of apoA-IV. Accordingly, it was discovered that the degree of improvement of glucose tolerance was dependent on the dose of apoA-IV administered, with higher doses resulting in improved glucose tolerance.

Example 3: Specificity of ApoA-IV in Restoring Glucose Tolerance in ApoA-IV Knockout Mice Experimental Protocol.

In order to assess the specificity of apoA-IV, we administered apolipoprotein AI (hereinafter "apoA-I") to apoA-IV KO mice. ApoA-I is a protein made by the small intestinal epithelial cells which also produce apoA-IV. ApoA-I shares many of the functions of apoA-IV. ApoA-IV KO mice were injected intraperitoneally with a dose of 1 µg/g by weight of apoA-I. ApoA-IV KO mice were also injected intraperitoneally with saline solution to serve as a control. Following injection with apoA-I or saline solution, glucose tolerance tests were conducted at three months of age as previously discussed. Specifically, glucose tolerance tests were conducted about two hours following injection with apoA-I or saline solution.

Experimental Results.

Figure 5:
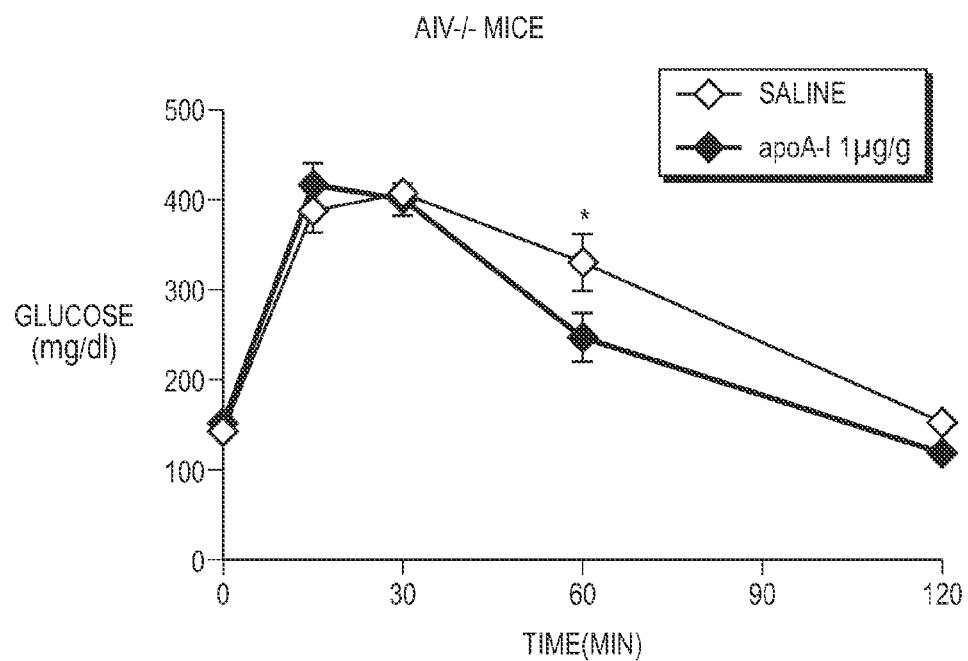
FIG. 5 is a graph of plasma glucose (mg/dL) with respect to time (min) in apolipoprotein A-IV knockout mice following the intraperitoneal administration of recombinant apolipoprotein A-I or saline solution for an intraperitoneal glucose tolerance test.

As shown in FIG. 5, the administration of apoA-I to apoA-IV KO mice failed to restore or improve glucose tolerance.

Example 4: Mechanism of Restoration of Glucose Tolerance in ApoA-IV Knockout Mice Experimental Protocol.

In order to assess the mechanism by which ApoA-IV improves glucose tolerance in apoA-IV KO mice, we measured glucose-induced insulin secretion in apoA-IV KO mice. More specifically, we measured glucose-induced insulin secretion during glucose tolerance tests at three months of age as previously discussed. In this study, apoA-IV KO mice were injected intraperitoneally with a dose of about 1 µg/g by weight of mouse apoA-IV two hours prior to conducting the glucose tolerance tests. ApoA-IV KO mice were injected with saline solution about two hours prior to conducting glucose tolerance tests to serve as a control.

Experimental Results.

Figure 6:
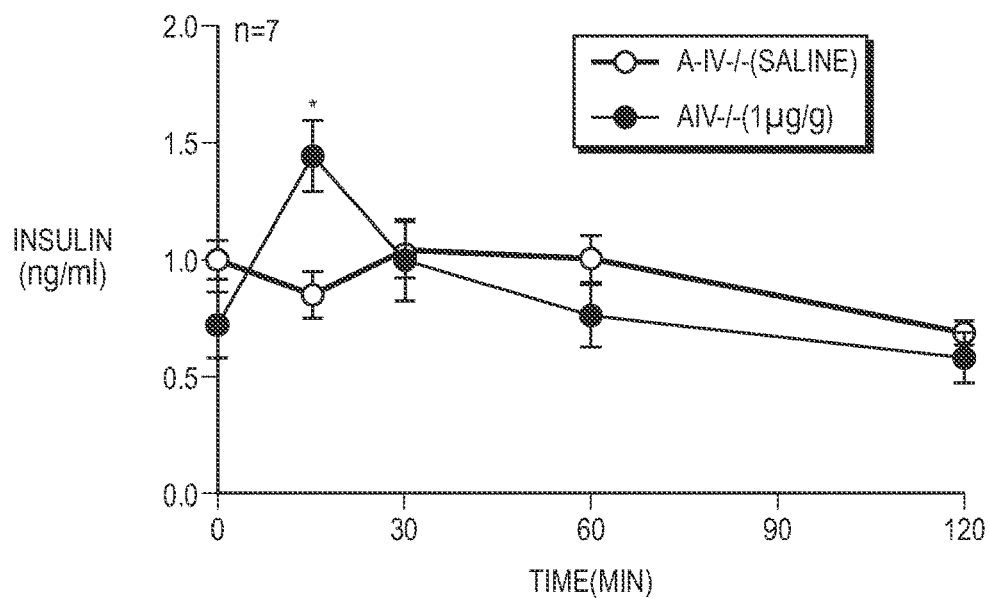
FIG. 6 is a graph of insulin secretion (ng/mL) with respect to time (min) in apolipoprotein A-IV knockout mice following the intraperitoneal administration of recombinant apolipoprotein A-I or saline solution.

As shown in FIG. 6, phase I insulin secretion was absent in apoA-IV KO mice injected with saline solution. However, as shown in FIG. 6, phase I insulin secretion was restored in apoA-IV KO mice when apoA-IV was injected intraperitoneally two hours prior to performing the glucose tolerance tests.

Example 5: Efficacy of ApoA-IV in ApoA-IV Knockout and Wild-Type Mice on High Fat Diets Experimental Protocol.

ApoA-IV KO and WT mice were chronically fed a high-fat semi-purified, nutritionally complete experimental diets (AIN-93M) purchased from Dyets (Bethlehem, Pa.) for 10 weeks. The high-fat diets contain about 20 g of fat (i.e. about 19 g of butter fat and 1 g of soybean oil to provide essential fatty acids) per 100 g of diet. The apoA-IV KO and WT mice were housed in individual tub cages with corncob bedding in a temperature—(about 22±1° C.) and light—(about 12 h light/12 dark) controlled vivarium. Glucose tolerance tests were performed at three months of age as previously discussed. Prior to performing the glucose tolerance tests, apoA-IV KO mice and WT mice were fasted for five hours. In the glucose tolerance tests, the apoA-IV KO mice and WT mice were injected intraperitoneally with a dose of about 2 mg/g body weight of glucose.

Experimental Results.

Figure 7:
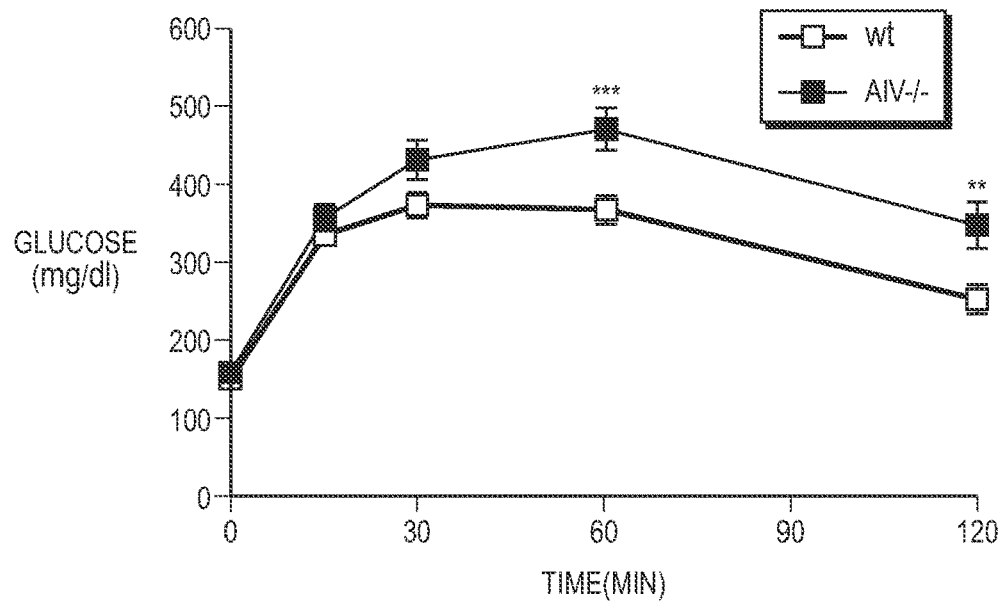
FIG. 7 is graph of plasma glucose (mg/mL) with respect to time (min) in apolipoprotein A-IV knockout and wild-type mice on a chronically high-fat diet for an intraperitoneal glucose tolerance test.

As shown in FIG. 7, apoA-IV KO mice displayed greater glucose intolerance relative to the WT mice. Specifically, FIG. 7 shows that plasma glucose levels in WT mice were lower than plasma glucose levels in apoA-IV KO mice for two hours following intraperitoneal injection with glucose.

Example 6: Restoration of Glucose Tolerance in ApoA-IV Knockout and Wild-Type Mice on High Fat Diets Experimental Protocol.

A series of studies were performed related to the administration of apoA-IV to apoA-IV KO and WT mice on high-fat diets for 14 weeks at three months of age (20% by weight of fat, 19% of butter fat and 1% of safflower oil). Specifically, apoA-IV KO and WT mice were injected intraperitoneally with a dose of about 1 µg/g body weight of mouse apoA-IV. ApoA-IV KO and WT mice were also injected intraperitoneally with saline solution to serve as a control. Following injection with apoA-IV or saline solution, glucose tolerance tests were conducted. Specifically, glucose tolerance tests were conducted two hours following injection with apoA-IV or saline solution.

Experimental Results.

Figure 8:
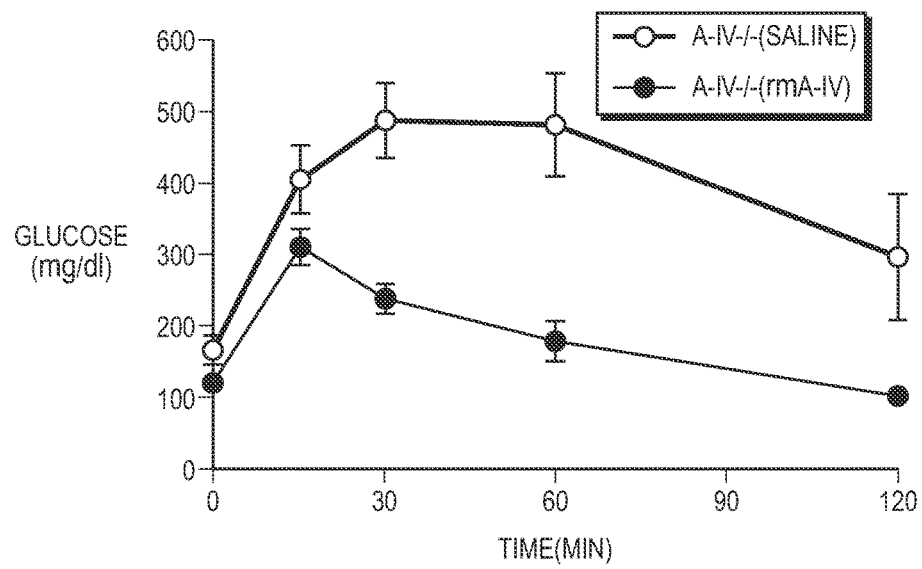
FIG. 8 is a graph of plasma glucose (mg/mL) with respect to time (min) in apolipoprotein A-IV knockout mice on a chronically high-fat diet following the intraperitoneal administration of recombinant mouse apolipoprotein A-IV (1 µg/g) or saline solution for an intraperitoneal glucose tolerance test.

As shown in FIG. 8, the administration of apoA-IV in apoA-IV KO mice significantly improved glucose tolerance. Specifically, FIG. 8 shows that plasma glucose levels in apoA-IV KO mice injected with apoA-IV were lower than plasma glucose levels in apoA-IV KO mice injected with saline solution. [the previous sentence is redundant since the next sentence describes the same thing. Although the data is not included herein, it was also discovered that the administration of apoA-IV in WT mice fed chronically a high fat diet also significantly improved glucose tolerance.

Example 7: Restoration of Glucose Tolerance in Mice with Type 2 Diabetes

Experimental Protocol.

In order to confirm that apoA-IV is effective in promoting glucose tolerance in animals with type 2 diabetes, heterozygous KK Cg-A/J (hereinafter "Cg-A/J") mice were obtained from Jackson Laboratories (Bar Harbor, Me.). Cg-A/J mice develop hyperglycemia, hyperinsulinemia, obesity, and glucose intolerance by eight weeks of age. The main cause of diabetes in these mice is insulin resistance produced by the polygenic interactions with the $A^y$ mutation, which encodes the agouti related protein and antagonist of the melanocortin-IV receptor. The Cg-A/J mice were fed chow diet. Additionally, there was a marked increase in blood glucose from ten to fourteen weeks of feeding the chow diet.

At fourteen weeks of age, the Cg-A/J mice were administered either mouse apoA-IV (about 1 μg/g body weight) or saline solution (to serve as a control) via intraperitoneal injection. Plasma glucose was then determined at about 0, 0.5, 1, 2, 3, 4, 5, 7, 11, and 24 hours.

Experimental Results.

Figure 9:
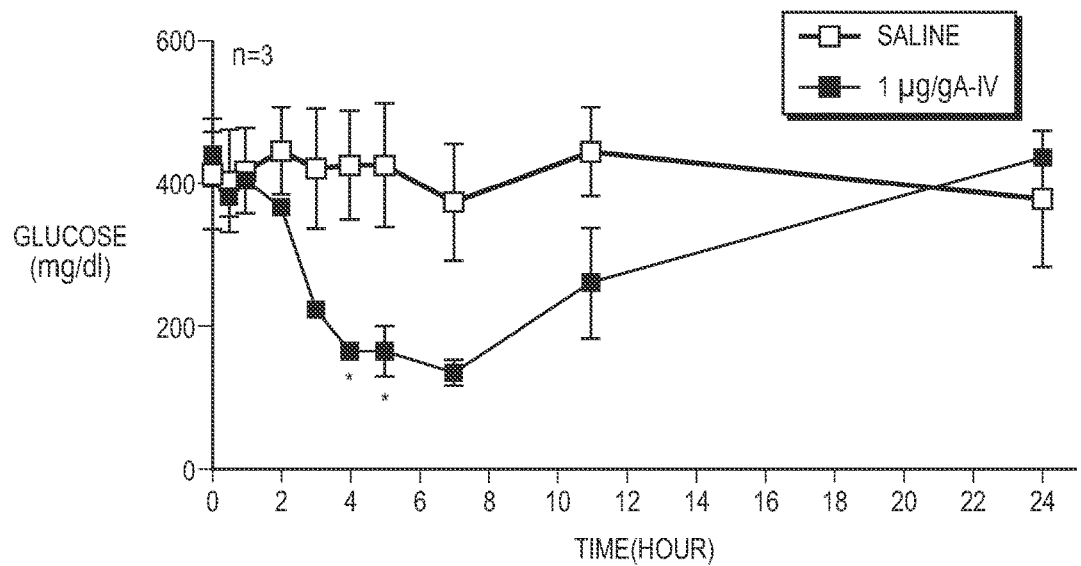
FIG. 9 is a graph of plasma glucose (mg/dL) with respect to time (h) in diabetic mice following the intraperitoneal administration of recombinant mouse apolipoprotein A-IV (1 µg/g) or saline solution for an intraperitoneal glucose tolerance test.

As shown in FIG. 9, apoA-IV has a marked effect in lowering the blood sugar level of the Cg-A/J mice relative to the saline control. While the Cg-A/J mice injected with saline solution maintained a steady plasma glucose level throughout the 24 hour period of study, the Cg-A/J mice injected with apoA-IV experienced a decrease in plasma glucose for over 10 hours, and, during most of this period, the plasma glucose level was comparable to the C57BL/6J animals we have been studying. From this study, we conclude that the administration of apoA-IV is effective in lowering the plasma glucose in Cg-A/J mice.

Example 8: Level of Serum Amyloid P Component in ApoA-IV KO, ApoA-I KO, and WT Mice Experimental Protocol.

A series of studies were performed in related to determining the level of serum amyloid A protein component (hereinafter "SAP") in apoA-IV KO, apoA-I KO, and WT mice on atherogenic diets. The apoA-IV KO, apoA-I KO, and WT mice were obtained from the University of Cincinnati. SAP is a serum form of amyloid P component (hereinafter "AP"), a 25 kDa pentameric protein first identified as the pentagonal constituent of in vivo pathological deposits called amyloid. SAP behaves like C-reactive protein in humans. Specifically, the level of plasma SAP in apoA-IV KO, apoA-I KO, and WT mice was determined in apoA-IV KO, apoA-I KO, and WT mice after 12 weeks on an atherogenic diet. The level of plasma SAP was determined via Western blot analysis.

Experimental Results.

Figure 10:
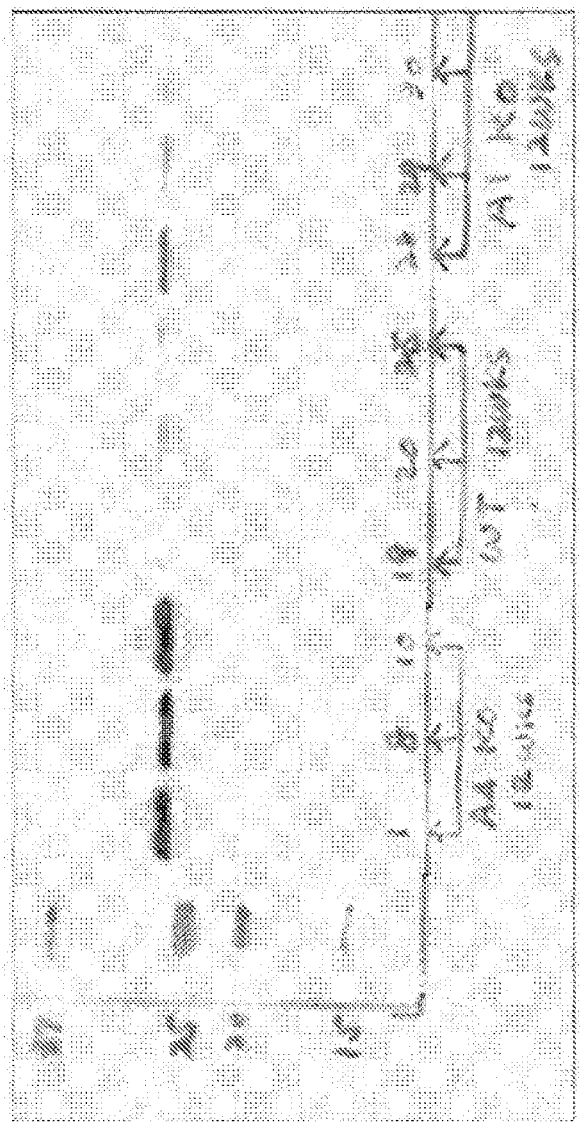
FIG. 10 depicts the results of a Western blot analysis of the level of serum amyloid A protein component in apolipoprotein A-IV knockout mice, wild-type mice, and apolipoprotein A-I knockout mice.

As shown in FIG. 10, the level of SAP in apoA-IV KO mice (corresponding to mouse numbers 1, 8, and 10) increased relative to the level of SAP in apoA-I KO mice (corresponding to mouse numbers 28, 29, and 30) and WT mice (corresponding to mouse numbers 19, 20, and 25).

For the purposes of describing and defining the present disclosure it is noted that the terms "about" and "substantially" are utilized herein to represent the inherent degree of uncertainty that may be attributed to any quantitative comparison, value, measurement, or other representation. The terms "about" and "substantially" are also utilized herein to represent the degree by which a quantitative representation may vary from a stated reference without resulting in a change in the basic function of the subject matter at issue.

The above description and drawings are only to be considered illustrative of exemplary embodiments, which achieve the features and advantages of the present disclosure. Modification and substitutions the features and steps described can be made without departing from the intent and scope of the present disclosure. Accordingly, the disclosure is not to be considered as being limited by the foregoing description and drawings, but is only limited by the scope of the appended claims.

Example 9: Human ApoA-IV Lowers Blood Glucose Levels in Wild-Type Mice Undergoing Intraperitoneal Glucose Tolerance Testing Experimental Protocol.

Studies were performed to determine whether administration of human apoA-IV to wild type mice would affect blood glucose levels in mice undergoing glucose tolerance testing.

Three month old wild type mice were injected intraperitoneally with doses of about 1 μg/g by weight of human apoA-IV. As a control, another group of wild type mice was injected intraperitoneally with saline solution. Following injection with human apoA-IV or saline solution, glucose tolerance tests were conducted. Specifically, glucose tolerance tests were conducted about two hours following injection with apoA-IV or saline solution and after five hours of fasting. Tail blood was collected and measure by glucometer.

Experimental Results.

Figure 12:
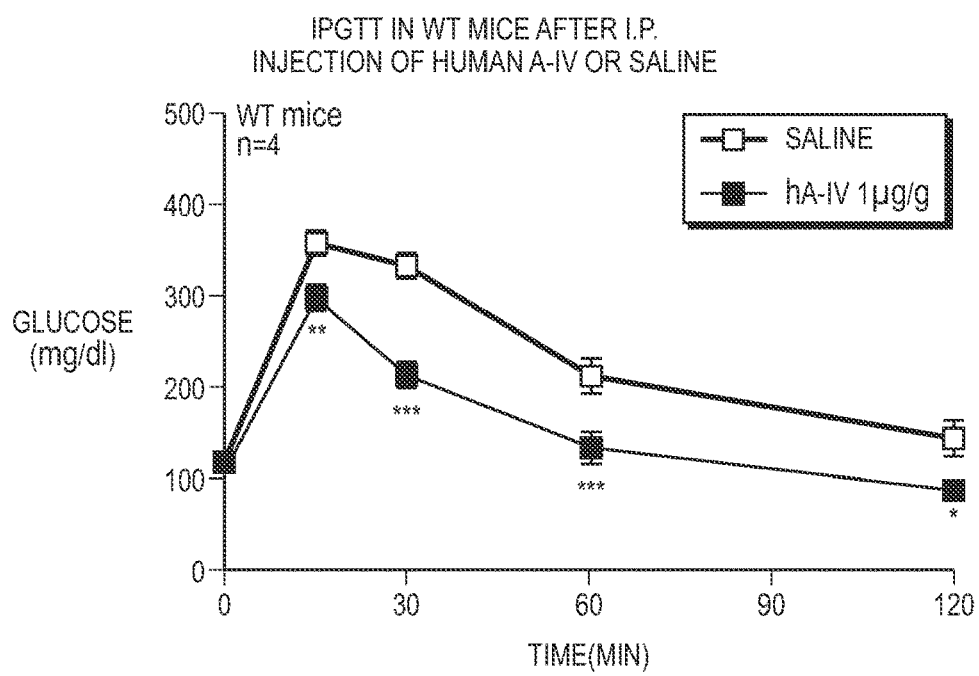
FIG. 12. is a graph of plasma glucose (mg/dL) with respect to time (min) in wild type mice following the intraperitoneal administration of 1.0 µg/g human apolipoprotein A-IV or saline solution during an intraperitoneal glucose tolerance test.

As shown in FIG. 12, human apoA-IV was effective in lowering blood glucose in wild type mice undergoing glucose tolerance testing.

Example 10: Effect of Mouse ApoA-IV in Wild-Type Female Mice Undergoing Intraperitoneal Glucose Tolerance Testing Experimental Protocol.

Studies were performed to determine whether administration of mouse apoA-IV to female wild type mice would affect blood glucose levels in mice undergoing glucose tolerance testing.

Three month old female wild type mice were injected intraperitoneally with doses of about 1 μg/g by weight of mouse apoA-IV. As a control, another group of female wild type mice were injected intraperitoneally with saline solution. Following injection with human apoA-IV or saline solution, glucose tolerance tests were conducted. Specifically, glucose tolerance tests were conducted about two hours following injection with apoA-IV or saline solution and after five hours of fasting. Tail blood was collected and measure by glucometer.

Experimental Results.

Figure 13:
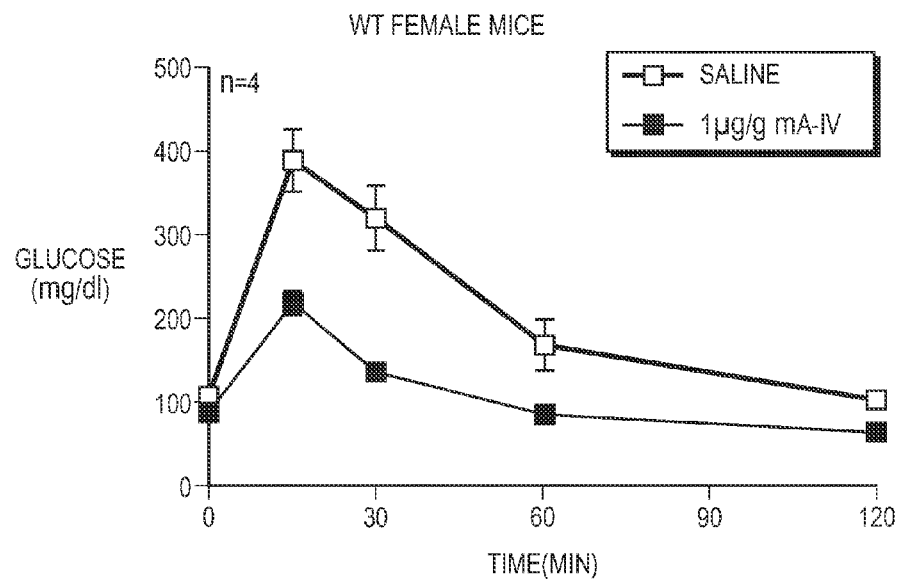
FIG. 13 is a graph of plasma glucose (mg/dL) with respect to time (min) in female wild type mice following the intraperitoneal administration of 1.0 µg/g recombinant mouse apolipoprotein A-IV or saline solution during an intraperitoneal glucose tolerance test.

As shown in FIG. 13, mouse apoA-IV was effective in lowering blood glucose in wild type female mice undergoing glucose tolerance testing.

Example 11: Human ApoA-IV Stimulates Insulin Release in Human Islets

High purity human islets were provided by University of Virginia, Axon Cells. Islets were cultured in RPMI 1640, containing 10% FBS and 11 mM glucose at 37° C. in a humidified atmosphere of 95% air and 5% $CO_2$ for 48 hours.

Four Groups of 50 IEQ islets were then pre-incubated at 37° C. for 1 h in regular KRB (129 mM NaCl, 4.8 mM KCl, 2.5 mM CaCl$_2$, 1.2 mM MgSO$_4$, 1.2 mM KH$_2$PO$_4$, 5 mM NaHCO$_3$, 10 mM HEPES and 0.2% BSA) containing 3.0 mM glucose. Islets in the first two groups were then incubated in regular KRB containing 3.0 mM glucose for an hour in the presence or absence of 10 µg/ml human A-IV and were further incubated with 20 mM glucose for an additional hour in the presence or absence of 10 µg/ml human A-IV. Islets in the last two groups were incubated in 30 mM KCl KRB (103.8 mM NaCl, 30 mM KCl, 2.5 mM CaCl$_2$, 1.2 mM MgSO$_4$, 1.2 mM KH$_2$PO$_4$, 5 mM NaHCO$_3$, 10 mM HEPES and 0.2% BSA) plus 250 µmol/l diazoxide containing 3.0 mM glucose for an hour in the presence or absence of 10 µg/ml human A-IV and were further incubated with 20 mM glucose for an additional hour in the presence or absence of 10 µg/ml human A-IV. Media were collected at the end of each one-hour incubation. Insulin levels were measured by ELISA kit (Millipore).

Figure 14:
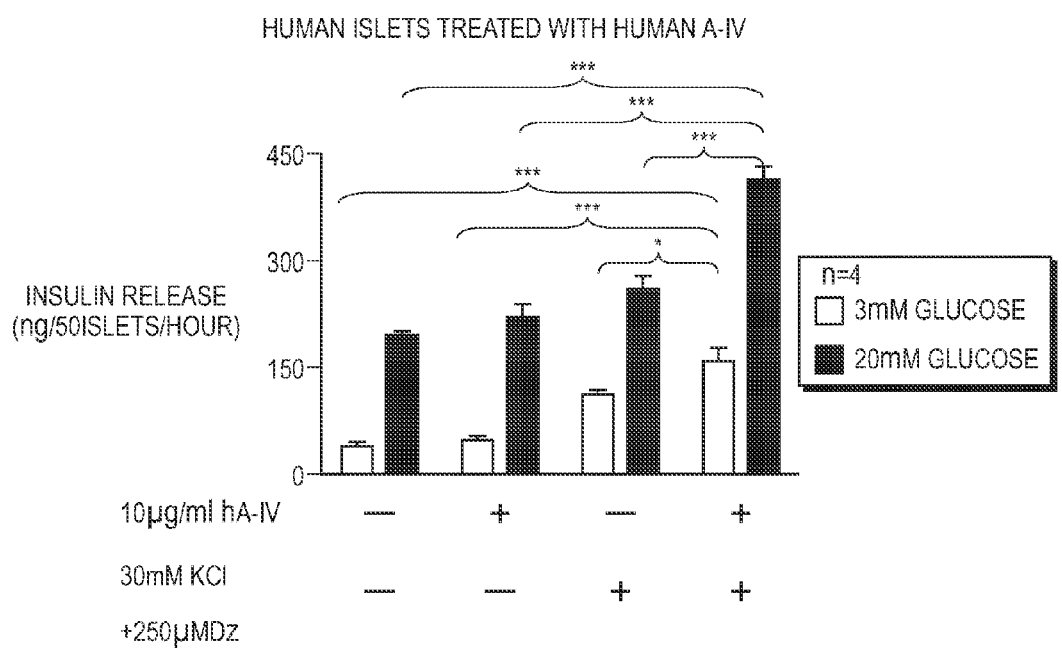
FIG. 14 is a bar graph showing the effect of 10 µg/g human apoA-IV on human islets depolarized by 30 mM KCl and 250 µM diazoxide in the presence of 3 mM or 20 mM glucose.

As can be seen from FIG. 14, when the human islets were maximally depolarized by 30 mM KCl plus 250 µM diazoxide, 10 µg/ml hA-IV showed a significant stimulatory effect on insulin secretion.

Example 12: Preparation of Unglycosylated ApoA-IV

Human and mouse apoA-IV cDNA was contained in a pSP65 maintenance vector, and an Afl III restriction site was engineered immediately 5' of the coding sequence for the mature apoA-IV protein. The gene was excised from the maintenance vector and ligated into the pET30 expression vector. The construct was transfected into *E. Coli* BL-21 (DE3) cells and grown in Luria-Bertani cultures supplemented with kanamycin (30 µg/ml) at 37° C. After induction of apoA-IV protein synthesis in the cells, the cells were harvested and sonicated. ApoA-IV protein from the lysate was purified by His-bind affinity column chromatography and dialysis. The resultant apoA-IV protein was diluted to a final concentration of 1.0 mg/ml in saline.

INCORPORATION BY REFERENCE

The contents of all references and patents cited herein are hereby incorporated by reference in their entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

---

SEQUENCE LISTING

```
<160> NUMBER OF SEQ ID NOS: 51

<210> SEQ ID NO 1
<211> LENGTH: 376
<212> TYPE: PRT
<213> ORGANISM: Homo sapiens

<400> SEQUENCE: 1

Glu Val Ser Ala Asp Gln Val Ala Thr Val Met Trp Asp Tyr Phe Ser
1               5                   10                  15

Gln Leu Ser Asn Asn Ala Lys Glu Ala Val Glu His Leu Gln Lys Ser
            20                  25                  30

Glu Leu Thr Gln Gln Leu Asn Ala Leu Phe Gln Asp Lys Leu Gly Glu
        35                  40                  45

Val Asn Thr Tyr Ala Gly Asp Leu Gln Lys Lys Leu Val Pro Phe Ala
    50                  55                  60

Thr Glu Leu His Glu Arg Leu Ala Lys Asp Ser Glu Lys Leu Lys Glu
65                  70                  75                  80

Glu Ile Gly Lys Glu Leu Glu Glu Leu Arg Ala Arg Leu Leu Pro His
                85                  90                  95

Ala Asn Glu Val Ser Gln Lys Ile Gly Asp Asn Leu Arg Glu Leu Gln
            100                 105                 110

Gln Arg Leu Glu Pro Tyr Ala Asp Gln Leu Arg Thr Gln Val Asn Thr
        115                 120                 125

Gln Ala Glu Gln Leu Arg Arg Gln Leu Thr Pro Tyr Ala Gln Arg Met
    130                 135                 140

Glu Arg Val Leu Arg Glu Asn Ala Asp Ser Leu Gln Ala Ser Leu Arg
145                 150                 155                 160

Pro His Ala Asp Glu Leu Lys Ala Lys Ile Asp Gln Asn Val Glu Glu
                165                 170                 175

Leu Lys Gly Arg Leu Thr Pro Tyr Ala Asp Glu Phe Lys Val Lys Ile
```

```
            180                 185                 190
Asp Gln Thr Val Glu Glu Leu Arg Arg Ser Leu Ala Pro Tyr Ala Gln
            195                 200                 205

Asp Thr Gln Glu Lys Leu Asn His Gln Leu Glu Gly Leu Thr Phe Gln
        210                 215                 220

Met Lys Lys Asn Ala Glu Glu Leu Lys Ala Arg Ile Ser Ala Ser Ala
225                 230                 235                 240

Glu Glu Leu Arg Gln Arg Leu Ala Pro Leu Ala Glu Asp Val Arg Gly
                245                 250                 255

Asn Leu Arg Gly Asn Thr Glu Gly Leu Gln Lys Ser Leu Ala Glu Leu
            260                 265                 270

Gly Gly His Leu Asp Gln Gln Val Glu Glu Phe Arg Arg Val Glu
        275                 280                 285

Pro Tyr Gly Glu Asn Phe Asn Lys Ala Leu Val Gln Gln Met Glu Gln
                290                 295                 300

Leu Arg Gln Lys Leu Gly Pro His Ala Gly Asp Val Glu Gly His Leu
305                 310                 315                 320

Ser Phe Leu Glu Lys Asp Leu Arg Asp Lys Val Asn Ser Phe Phe Ser
                325                 330                 335

Thr Phe Lys Glu Lys Glu Ser Gln Asp Lys Thr Leu Ser Leu Pro Glu
            340                 345                 350

Leu Glu Gln Gln Gln Gln Gln Gln Glu Gln Gln Glu Gln Val
                355                 360                 365

Gln Met Leu Ala Pro Leu Glu Ser
        370                 375

<210> SEQ ID NO 2
<211> LENGTH: 361
<212> TYPE: PRT
<213> ORGANISM: Mus musculus

<400> SEQUENCE: 2

Glu Val Thr Ser Asp Gln Val Ala Asn Val Val Trp Asp Tyr Phe Thr
1               5                   10                  15

Gln Leu Ser Asn Asn Ala Lys Glu Ala Val Gln Phe Gln Lys Thr
            20                  25                  30

Asp Val Gln Gln Leu Ser Thr Leu Phe Ala Ser Thr Tyr Ala Asp Gly
        35                  40                  45

Val His Asn Lys Leu Val Pro Phe Val Val Gln Leu Ser Gly His Leu
    50                  55                  60

Ala Gln Glu Thr Glu Arg Val Lys Glu Glu Ile Lys Lys Glu Leu Glu
65                  70                  75                  80

Asp Leu Arg Asp Arg Lys Thr Gln Thr Phe Gly Glu Asn Met Gln Lys
                85                  90                  95

Leu Gln Glu His Leu Lys Pro Tyr Ala Val Asp Leu Gln Asp Gln Ile
            100                 105                 110

Asn Thr Gln Thr Gln Glu Met Lys Leu Gln Leu Thr Pro Tyr Ile Gln
        115                 120                 125

Arg Met Gln Thr Thr Ile Lys Glu Asn Val Asp Asn Leu His Thr Ser
130                 135                 140

Met Met Pro Leu Ala Thr Asn Leu Lys Asp Lys Phe Asn Arg Asn Met
145                 150                 155                 160

Glu Glu Leu Lys Gly His Leu Thr Pro Arg Ala Asn Glu Leu Lys Ala
                165                 170                 175
```

```
Thr Ile Asp Gln Asn Leu Glu Asp Leu Arg Arg Ser Leu Ala Pro Leu
            180                 185                 190

Thr Val Gly Val Gln Glu Lys Leu Asn His Gln Met Glu Gly Leu Ala
        195                 200                 205

Phe Gln Met Lys Lys Asn Ala Glu Glu Leu Gln Thr Lys Val Ser Ala
    210                 215                 220

Lys Ile Asp Gln Leu Gln Lys Asn Leu Ala Pro Leu Val Glu Asp Val
225                 230                 235                 240

Gln Ser Lys Val Lys Gly Asn Thr Glu Gly Leu Gln Lys Ser Leu Glu
                245                 250                 255

Asp Leu Asn Arg Gln Leu Glu Gln Gln Val Glu Glu Phe Arg Arg Thr
            260                 265                 270

Val Glu Pro Met Gly Glu Met Phe Asn Lys Ala Leu Val Gln Gln Leu
        275                 280                 285

Glu Gln Phe Arg Gln Gln Leu Gly Pro Asn Ser Gly Glu Val Glu Ser
    290                 295                 300

His Leu Ser Phe Leu Glu Lys Ser Leu Arg Glu Lys Val Asn Ser Phe
305                 310                 315                 320

Met Ser Thr Leu Glu Lys Lys Gly Ser Pro Asp Gln Pro Gln Ala Leu
                325                 330                 335

Pro Leu Pro Glu Gln Ala Gln Glu Gln Ala Gln Glu Gln Ala Gln Glu
            340                 345                 350

Gln Val Gln Pro Lys Pro Leu Glu Ser
                355                 360

<210> SEQ ID NO 3
<211> LENGTH: 377
<212> TYPE: PRT
<213> ORGANISM: Artificial Sequence
<220> FEATURE:
<223> OTHER INFORMATION: Synthetic Polypeptide

<400> SEQUENCE: 3

Gly Glu Val Ser Ala Asp Gln Val Ala Thr Val Met Trp Asp Tyr Phe
1               5                   10                  15

Ser Gln Leu Ser Asn Asn Ala Lys Glu Ala Val Glu His Leu Gln Lys
            20                  25                  30

Ser Glu Leu Thr Gln Gln Leu Asn Ala Leu Phe Gln Asp Lys Leu Gly
        35                  40                  45

Glu Val Asn Thr Tyr Ala Gly Asp Leu Gln Lys Lys Leu Val Pro Phe
    50                  55                  60

Ala Thr Glu Leu His Glu Arg Leu Ala Lys Asp Ser Glu Lys Leu Lys
65                  70                  75                  80

Glu Glu Ile Gly Lys Glu Leu Glu Glu Leu Arg Ala Arg Leu Leu Pro
                85                  90                  95

His Ala Asn Glu Val Ser Gln Lys Ile Gly Asp Asn Leu Arg Glu Leu
            100                 105                 110

Gln Gln Arg Leu Glu Pro Tyr Ala Asp Gln Leu Arg Thr Gln Val Asn
        115                 120                 125

Thr Gln Ala Glu Gln Leu Arg Arg Gln Leu Thr Pro Tyr Ala Gln Arg
    130                 135                 140

Met Glu Arg Val Leu Arg Glu Asn Ala Asp Ser Leu Gln Ala Ser Leu
145                 150                 155                 160

Arg Pro His Ala Asp Glu Leu Lys Ala Lys Ile Asp Gln Asn Val Glu
                165                 170                 175
```

```
Glu Leu Lys Gly Arg Leu Thr Pro Tyr Ala Asp Glu Phe Lys Val Lys
            180                 185                 190

Ile Asp Gln Thr Val Glu Glu Leu Arg Arg Ser Leu Ala Pro Tyr Ala
        195                 200                 205

Gln Asp Thr Gln Glu Lys Leu Asn His Gln Leu Glu Gly Leu Thr Phe
    210                 215                 220

Gln Met Lys Lys Asn Ala Glu Glu Leu Lys Ala Arg Ile Ser Ala Ser
225                 230                 235                 240

Ala Glu Glu Leu Arg Gln Arg Leu Ala Pro Leu Ala Glu Asp Val Arg
                245                 250                 255

Gly Asn Leu Arg Gly Asn Thr Glu Gly Leu Gln Lys Ser Leu Ala Glu
            260                 265                 270

Leu Gly Gly His Leu Asp Gln Gln Val Glu Glu Phe Arg Arg Arg Val
        275                 280                 285

Glu Pro Tyr Gly Glu Asn Phe Asn Lys Ala Leu Val Gln Gln Met Glu
    290                 295                 300

Gln Leu Arg Gln Lys Leu Gly Pro His Ala Gly Asp Val Glu Gly His
305                 310                 315                 320

Leu Ser Phe Leu Glu Lys Asp Leu Arg Asp Lys Val Asn Ser Phe Phe
                325                 330                 335

Ser Thr Phe Lys Glu Lys Glu Ser Gln Asp Lys Thr Leu Ser Leu Pro
            340                 345                 350

Glu Leu Glu Gln Gln Gln Glu Gln Gln Gln Gln Gln Gln Gln Glu Gln
        355                 360                 365

Val Gln Met Leu Ala Pro Leu Glu Ser
    370                 375

<210> SEQ ID NO 4
<211> LENGTH: 377
<212> TYPE: PRT
<213> ORGANISM: Homo sapiens
<220> FEATURE:
<221> NAME/KEY: VARIANT
<222> LOCATION: (1)..(1)
<223> OTHER INFORMATION: X is G, A, V or absent
<220> FEATURE:
<221> NAME/KEY: VARIANT
<222> LOCATION: (166)..(166)
<223> OTHER INFORMATION: X is E or K
<220> FEATURE:
<221> NAME/KEY: VARIANT
<222> LOCATION: (348)..(348)
<223> OTHER INFORMATION: X is T or S
<220> FEATURE:
<221> NAME/KEY: VARIANT
<222> LOCATION: (361)..(361)
<223> OTHER INFORMATION: X is Q or H

<400> SEQUENCE: 4

Xaa Glu Val Ser Ala Asp Gln Val Ala Thr Val Met Trp Asp Tyr Phe
1               5                   10                  15

Ser Gln Leu Ser Asn Asn Ala Lys Glu Ala Val Glu His Leu Gln Lys
            20                  25                  30

Ser Glu Leu Thr Gln Gln Leu Asn Ala Leu Phe Gln Asp Lys Leu Gly
        35                  40                  45

Glu Val Asn Thr Tyr Ala Gly Asp Leu Gln Lys Lys Leu Val Pro Phe
    50                  55                  60

Ala Thr Glu Leu His Glu Arg Leu Ala Lys Asp Ser Glu Lys Leu Lys
65                  70                  75                  80

Glu Glu Ile Gly Lys Glu Leu Glu Glu Leu Arg Ala Arg Leu Leu Pro
```

```
            85                  90                  95
His Ala Asn Glu Val Ser Gln Lys Ile Gly Asp Asn Leu Arg Glu Leu
        100                 105                 110

Gln Gln Arg Leu Glu Pro Tyr Ala Asp Gln Leu Arg Thr Gln Val Asn
        115                 120                 125

Thr Gln Ala Glu Gln Leu Arg Arg Gln Leu Thr Pro Tyr Ala Gln Arg
    130                 135                 140

Met Glu Arg Val Leu Arg Glu Asn Ala Asp Ser Leu Gln Ala Ser Leu
145                 150                 155                 160

Arg Pro His Ala Asp Xaa Leu Lys Ala Lys Ile Asp Gln Asn Val Glu
                165                 170                 175

Glu Leu Lys Gly Arg Leu Thr Pro Tyr Ala Asp Glu Phe Lys Val Lys
            180                 185                 190

Ile Asp Gln Thr Val Glu Glu Leu Arg Arg Ser Leu Ala Pro Tyr Ala
        195                 200                 205

Gln Asp Thr Gln Glu Lys Leu Asn His Gln Leu Glu Gly Leu Thr Phe
    210                 215                 220

Gln Met Lys Lys Asn Ala Glu Glu Leu Lys Ala Arg Ile Ser Ala Ser
225                 230                 235                 240

Ala Glu Glu Leu Arg Gln Arg Leu Ala Pro Leu Ala Glu Asp Val Arg
                245                 250                 255

Gly Asn Leu Arg Gly Asn Thr Glu Gly Leu Gln Lys Ser Leu Ala Glu
            260                 265                 270

Leu Gly Gly His Leu Asp Gln Gln Val Glu Glu Phe Arg Arg Arg Val
        275                 280                 285

Glu Pro Tyr Gly Glu Asn Phe Asn Lys Ala Leu Val Gln Gln Met Glu
    290                 295                 300

Gln Leu Arg Gln Lys Leu Gly Pro His Ala Gly Asp Val Glu Gly His
305                 310                 315                 320

Leu Ser Phe Leu Glu Lys Asp Leu Arg Asp Lys Val Asn Ser Phe Phe
                325                 330                 335

Ser Thr Phe Lys Glu Lys Glu Ser Gln Asp Lys Xaa Leu Ser Leu Pro
            340                 345                 350

Glu Leu Glu Gln Gln Gln Gln Xaa Gln Gln Gln Gln Gln Gln Glu Gln
        355                 360                 365

Val Gln Met Leu Ala Pro Leu Glu Ser
    370                 375

<210> SEQ ID NO 5
<211> LENGTH: 1125
<212> TYPE: DNA
<213> ORGANISM: Homo sapiens

<400> SEQUENCE: 5
gtcagtgctg accaggtggc cacagtgatg tgggactact tcagccagct gagcaacaat      60
gccaaggagg ccgtggaaca tctccagaaa tctgaactca cccagcaact caatgccctc     120
ttccaggaca aacttggaga agtgaacact tacgcaggtg acctgcagaa gaagctggtg     180
ccctttgcca ccgagctgca tgaacgcctg gccaaggact cggagaaact gaaggaggag     240
attgggaagg agctggagga gctgagggcc cggctgctgc ccatgccaa tgaggtgagc      300 cagaagatcg gggacaacct gcgagagctt cagcagcgcc tggagcccta cgcggaccag     360
ctgcgcaccc aggtcaacac gcaggccgag cagctgcggc gccagctgac cccctacgca     420
cagcgcatgg agagagtgct gcgggagaac gccgacagcc tgcaggcctc gctgaggccc     480
```

```
cacgccgacg agctcaaggc caagatcgac cagaacgtgg aggagctcaa gggacgcctt    540
acgccctacg ctgacgaatt caaagtcaag attgaccaga ccgtggagga gctgcgccgc    600
agcctggctc cctatgctca ggacacgcag gagaagctca accaccagct tgagggcctg    660
accttccaga tgaagaagaa cgccgaggag ctcaaggcca ggatctcggc cagtgccgag    720
gagctgcggc agaggctggc gcccttggcc gaggacgtgc gtggcaacct gaggggcaac    780
accgaggggc tgcagaagtc actggcagag ctgggtgggc acctggacca gcaggtggag    840
gagttccgac gccgggtgga gccctacggg gaaaacttca caaagccct ggtgcagcag    900 atggaacagc tcaggcagaa actgggcccc catgcggggg acgtggaagg ccacctgagc    960
ttcctggaga aggacctgag ggacaaggtc aactccttct tcagcacctt caaggagaaa   1020
gagagccagg acaagactct ctccctccct gagctcgagc aacagcagga acagcagcag   1080
gagcagcagc aggagcaggt gcagatgctg gccccctttgg agagc                   1125
```

<210> SEQ ID NO 6
<211> LENGTH: 396
<212> TYPE: PRT
<213> ORGANISM: Homo sapiens

<400> SEQUENCE: 6

```
Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255
```

-continued

```
Ser Ala Ser Ala Glu Glu Leu Arg Gln Arg Leu Ala Pro Leu Ala Glu
                260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
        290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Gln Gln Gln Gln Gln Gln Gln
    370                 375                 380

Gln Glu Gln Val Gln Met Leu Ala His Leu Glu Ser
385                 390                 395

<210> SEQ ID NO 7
<211> LENGTH: 396
<212> TYPE: PRT
<213> ORGANISM: Homo sapiens

<400> SEQUENCE: 7

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240
```

```
Leu Thr Phe Gln Met Lys Lys Asn Ala Glu Glu Leu Lys Ala Arg Ile
            245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
            370                 375                 380

Lys Glu Gln Val Gln Met Leu Ala Pro Leu Glu Ser
385                 390                 395
```

<210> SEQ ID NO 8
<211> LENGTH: 396
<212> TYPE: PRT
<213> ORGANISM: Homo sapiens

<400> SEQUENCE: 8

```
Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65              70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
```

```
            210                 215                 220
Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
                260                 265                 270

Asp Val Arg Gly Asn Leu Lys Gly Asn Thr Glu Gly Leu Gln Lys Ser
                275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
                340                 345                 350

Ser Phe Phe Ser Thr Phe Lys Glu Lys Glu Ser Gln Asp Lys Thr Leu
                355                 360                 365

Ser Leu Pro Glu Leu Glu Gln Gln Gln Gln Gln Lys Glu Gln Gln
            370                 375                 380

Gln Glu Gln Val Gln Met Leu Ala Pro Leu Glu Ser
385                 390                 395

<210> SEQ ID NO 9
<211> LENGTH: 396
<212> TYPE: PRT
<213> ORGANISM: Homo sapiens

<400> SEQUENCE: 9

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
                35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65              70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
                100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
        130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
                180                 185                 190
```

-continued

Asn Val Glu Glu Leu Lys Gly Arg Leu Thr Pro Tyr Ala Asp Glu Phe
195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
                260                 265                 270

Asp Val Arg Gly Asn Leu Lys Gly Asn Thr Glu Gly Leu Gln Lys Ser
                275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
                340                 345                 350

Ser Phe Phe Ser Thr Phe Lys Glu Lys Glu Ser Gln Asp Lys Thr Leu
                355                 360                 365

Ser Leu Pro Glu Leu Glu Gln Gln Gln Glu Gln Gln Gln Glu Gln Gln
                370                 375                 380

Gln Glu Gln Val Gln Met Leu Ala Pro Leu Glu Ser
385                 390                 395

<210> SEQ ID NO 10
<211> LENGTH: 396
<212> TYPE: PRT
<213> ORGANISM: Homo sapiens

<400> SEQUENCE: 10

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
                35                  40                  45

Leu Gln Lys Ser Glu Leu Thr Gln Gln Leu Asn Ala Leu Phe Gln Asp
50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
                100                 105                 110

Leu Leu Pro His Ala Asn Glu Val Ser Gln Lys Ile Gly Asp Asn Leu
                115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

```
Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Pro Glu Gln Gln Gln Glu Gln Gln
            370                 375                 380

Gln Glu Gln Val Gln Met Leu Ala Pro Leu Glu Ser
385                 390                 395

<210> SEQ ID NO 11
<211> LENGTH: 396
<212> TYPE: PRT
<213> ORGANISM: Homo sapiens

<400> SEQUENCE: 11

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
            130                 135                 140

Gln Val Asn Thr Gln Ala Glu Gln Leu Arg Arg Gln Leu Asp Pro Leu
```

```
            145                 150                 155                 160
        Ala Gln Arg Met Glu Arg Val Leu Arg Glu Asn Ala Asp Ser Leu Gln
                        165                 170                 175

Ala Ser Leu Arg Pro His Ala Asp Glu Leu Lys Ala Lys Ile Asp Gln
                        180                 185                 190

Asn Val Glu Glu Leu Lys Gly Arg Leu Thr Pro Tyr Ala Asp Glu Phe
                        195                 200                 205

Lys Val Lys Ile Asp Gln Thr Val Glu Glu Leu Arg Arg Ser Leu Ala
                        210                 215                 220

Pro Tyr Ala Gln Asp Thr Gln Glu Lys Leu Asn His Gln Leu Glu Gly
        225                 230                 235                 240

Leu Thr Phe Gln Met Lys Lys Asn Ala Glu Glu Leu Lys Ala Arg Ile
                        245                 250                 255

Ser Ala Ser Ala Glu Glu Leu Arg Gln Arg Leu Ala Pro Leu Ala Glu
                        260                 265                 270

Asp Val Arg Gly Asn Leu Lys Gly Asn Thr Glu Gly Leu Gln Lys Ser
                        275                 280                 285

Leu Ala Glu Leu Gly Gly His Leu Asp Gln Gln Val Glu Glu Phe Arg
                        290                 295                 300

Arg Arg Val Glu Pro Tyr Gly Glu Asn Phe Asn Lys Ala Leu Val Gln
        305                 310                 315                 320

Gln Met Glu Gln Leu Arg Gln Lys Leu Gly Pro His Ala Gly Asp Val
                        325                 330                 335

Glu Gly His Leu Ser Phe Leu Glu Lys Asp Leu Arg Asp Lys Val Asn
                        340                 345                 350

Ser Phe Phe Ser Thr Phe Lys Glu Lys Glu Ser Gln Asp Lys Ser Leu
                        355                 360                 365

Ser Leu Pro Glu Leu Glu Gln Gln Gln Gln Gln Gln Gln Gln Gln Gln
                        370                 375                 380

Gln Glu Gln Val Gln Met Leu Ala Pro Leu Glu Ser
        385                 390                 395

<210> SEQ ID NO 12
<211> LENGTH: 396
<212> TYPE: PRT
<213> ORGANISM: Homo sapiens

<400> SEQUENCE: 12

Met Phe Leu Lys Ala Val Val Leu Thr Leu Ala Leu Val Ala Val Ala
        1               5                   10                  15

Gly Ala Arg Ala Glu Val Ser Ala Asp Gln Val Ala Thr Val Met Trp
                        20                  25                  30

Asp Tyr Phe Ser Gln Leu Ser Asn Asn Ala Lys Glu Ala Val Glu His
                        35                  40                  45

Leu Gln Lys Ser Glu Leu Thr Gln Gln Leu Asn Ala Leu Phe Gln Asp
                        50                  55                  60

Lys Leu Gly Glu Val Asn Thr Tyr Ala Gly Asp Leu Gln Lys Lys Leu
        65                  70                  75                  80

Val Pro Phe Ala Thr Glu Leu His Glu Arg Leu Ala Lys Asp Ser Glu
                        85                  90                  95

Lys Leu Lys Glu Glu Ile Gly Lys Glu Leu Glu Glu Leu Arg Ala Arg
                        100                 105                 110

Leu Leu Pro His Ala Asn Glu Val Ser Gln Lys Ile Gly Asp Asn Leu
                        115                 120                 125
```

-continued

```
Arg Glu Leu Gln Gln Arg Leu Glu Pro Tyr Ala Asp Gln Leu Arg Thr
            130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ala Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 13
<211> LENGTH: 396
<212> TYPE: PRT
<213> ORGANISM: Homo sapiens

<400> SEQUENCE: 13

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110
```

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
        130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Tyr
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 14
<211> LENGTH: 396
<212> TYPE: PRT
<213> ORGANISM: Homo sapiens

<400> SEQUENCE: 14

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu

```
                    85                  90                  95
Lys Leu Lys Glu Glu Ile Gly Lys Glu Leu Glu Glu Leu Arg Ala Arg
                100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
        130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Met
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 15
<211> LENGTH: 396
<212> TYPE: PRT
<213> ORGANISM: Homo sapiens

<400> SEQUENCE: 15

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60
```

-continued

```
Lys Leu Gly Glu Val Asn Thr Tyr Ala Gly Asp Leu Gln Lys Lys Leu
 65                  70                  75                  80

Val Pro Phe Ala Thr Glu Leu His Glu Arg Leu Ala Lys Asp Ser Glu
                 85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly His Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395
```

<210> SEQ ID NO 16
<211> LENGTH: 396
<212> TYPE: PRT
<213> ORGANISM: Homo sapiens

<400> SEQUENCE: 16

```
Met Phe Leu Lys Ala Val Val Leu Thr Leu Ala Leu Val Ala Val Ala
  1               5                  10                  15

Gly Ala Arg Ala Glu Val Ser Ala Asp Gln Val Ala Thr Val Met Trp
             20                  25                  30

Asp Tyr Phe Ser Gln Leu Ser Asn Asn Ala Lys Glu Ala Val Glu His
         35                  40                  45
```

Leu Gln Lys Ser Glu Leu Thr Gln Gln Leu Asn Ala Leu Phe Gln Asp
            50                  55                  60

Lys Leu Gly Glu Val Asn Thr Tyr Ala Gly Asp Leu Gln Lys Lys Leu
 65                  70                  75                  80

Val Pro Phe Ala Thr Glu Leu His Glu Arg Leu Ala Lys Asp Ser Glu
                 85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
290                 295                 300

Arg Arg Val Glu Pro Tyr Arg Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
            370                 375                 380

Gln Glu Gln Val Gln Met Leu Ala Pro Leu Glu Ser
385                 390                 395

<210> SEQ ID NO 17
<211> LENGTH: 396
<212> TYPE: PRT
<213> ORGANISM: Homo sapiens

<400> SEQUENCE: 17

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp

```
            20                  25                  30
Asp Tyr Phe Ser Gln Leu Ser Asn Asn Ala Lys Glu Ala Val Glu His
        35                  40                  45
Leu Gln Lys Ser Glu Leu Thr Gln Gln Leu Asn Ala Leu Phe Gln Asp
    50                  55                  60
Lys Leu Gly Glu Val Asn Thr Tyr Ala Gly Asp Leu Gln Lys Lys Leu
65                  70                  75                  80
Val Pro Phe Ala Thr Glu Leu His Glu Arg Leu Ala Lys Asp Ser Glu
                85                  90                  95
Lys Leu Lys Glu Glu Ile Gly Lys Glu Leu Glu Glu Leu Arg Ala Arg
            100                 105                 110
Leu Leu Pro His Ala Asn Glu Val Ser Gln Lys Ile Gly Asp Asn Leu
        115                 120                 125
Arg Glu Leu Gln Gln Arg Leu Glu Pro Tyr Ala Asp Gln Leu Arg Thr
    130                 135                 140
Gln Val Asn Thr Gln Ala Glu Gln Leu Arg Arg Gln Leu Asp Pro Leu
145                 150                 155                 160
Ala Gln Arg Met Glu Arg Val Leu Arg Glu Asn Ala Asp Ser Leu Gln
                165                 170                 175
Ala Ser Leu Arg Pro His Ala Asp Glu Leu Lys Ala Lys Ile Asp Gln
            180                 185                 190
Asn Val Glu Glu Leu Lys Gly Arg Leu Thr Pro Tyr Ala Asp Glu Phe
        195                 200                 205
Lys Val Lys Ile Asp Gln Thr Val Glu Glu Leu Arg Arg Ser Leu Ala
    210                 215                 220
Pro Tyr Ala Gln Asp Thr Gln Glu Lys Leu Asn His Gln Leu Glu Gly
225                 230                 235                 240
Leu Thr Phe Gln Met Lys Lys Asn Ala Glu Glu Leu Lys Ala Arg Ile
                245                 250                 255
Ser Ala Ser Ala Glu Glu Leu Arg Gln Arg Leu Ala Pro Leu Ala Glu
            260                 265                 270
Asp Val Arg Gly Asn Leu Lys Gly Asn Thr Glu Gly Leu Gln Lys Ser
        275                 280                 285
Leu Ala Glu Leu Gly Gly His Leu Asp Gln Gln Val Glu Glu Phe Arg
    290                 295                 300
Arg Arg Leu Glu Pro Tyr Gly Glu Asn Phe Asn Lys Ala Leu Val Gln
305                 310                 315                 320
Gln Met Glu Gln Leu Arg Gln Lys Leu Gly Pro His Ala Gly Asp Val
                325                 330                 335
Glu Gly His Leu Ser Phe Leu Glu Lys Asp Leu Arg Asp Lys Val Asn
            340                 345                 350
Ser Phe Phe Ser Thr Phe Lys Glu Lys Glu Ser Gln Asp Lys Thr Leu
        355                 360                 365
Ser Leu Pro Glu Leu Glu Gln Gln Gln Glu Gln Gln Gln Glu Gln Gln
    370                 375                 380
Gln Glu Gln Val Gln Met Leu Ala Pro Leu Glu Ser
385                 390                 395

<210> SEQ ID NO 18
<211> LENGTH: 396
<212> TYPE: PRT
<213> ORGANISM: Homo sapiens

<400> SEQUENCE: 18
```

```
Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
    195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
    275                 280                 285

Leu Ala Glu Leu Gly Gly His Leu Asp Gln Gln Val Glu Glu Phe Arg
290                 295                 300

Cys Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
    355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 19
<211> LENGTH: 396
<212> TYPE: PRT
```

<213> ORGANISM: Homo sapiens

<400> SEQUENCE: 19

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Gln
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 20
<211> LENGTH: 396
<212> TYPE: PRT
<213> ORGANISM: Homo sapiens

<400> SEQUENCE: 20

```
Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Gly Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380
```

```
Gln Glu Gln Val Gln Met Leu Ala Pro Leu Glu Ser
385                 390                 395

<210> SEQ ID NO 21
<211> LENGTH: 396
<212> TYPE: PRT
<213> ORGANISM: Homo sapiens

<400> SEQUENCE: 21

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Met Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
```

Ser Leu Pro Glu Leu Glu Gln Gln Glu Gln Gln Glu Gln Gln
    355             360             365
Gln Glu Gln Val Gln Met Leu Ala Pro Leu Glu Ser
370             375             380
385             390             395

<210> SEQ ID NO 22
<211> LENGTH: 396
<212> TYPE: PRT
<213> ORGANISM: Homo sapiens

<400> SEQUENCE: 22

Met Phe Leu Lys Ala Val Val Leu Thr Leu Ala Leu Val Ala Val Ala
1               5                   10                  15
Gly Ala Arg Ala Glu Val Ser Ala Asp Gln Val Ala Thr Val Met Trp
                20                  25                  30
Asp Tyr Phe Ser Gln Leu Ser Asn Asn Ala Lys Glu Ala Val Glu His
            35                  40                  45
Leu Gln Lys Ser Glu Leu Thr Gln Gln Leu Asn Ala Leu Phe Gln Asp
        50                  55                  60
Lys Leu Gly Glu Val Asn Thr Tyr Ala Gly Asp Leu Gln Lys Lys Leu
65                  70                  75                  80
Val Pro Phe Ala Thr Glu Leu His Glu Arg Leu Ala Lys Asp Ser Glu
                85                  90                  95
Lys Leu Lys Glu Glu Ile Gly Lys Glu Leu Glu Glu Leu Arg Ala Arg
            100                 105                 110
Leu Leu Pro His Ala Asn Glu Val Ser Gln Lys Ile Gly Asp Asn Leu
        115                 120                 125
Arg Glu Leu Gln Gln Arg Leu Glu Pro Tyr Ala Asp Gln Leu Arg Thr
130                 135                 140
Gln Val Asn Thr Gln Ala Glu Gln Leu Arg Arg Gln Leu Asp Pro Leu
145                 150                 155                 160
Ala Gln Arg Met Glu Arg Val Leu Arg Glu Asn Ala Asp Ser Leu Gln
                165                 170                 175
Ala Ser Leu Arg Pro His Ala Asp Glu Leu Lys Ala Lys Ile Asp Gln
            180                 185                 190
Asn Val Glu Glu Leu Lys Gly Arg Leu Thr Pro Tyr Ala Asp Glu Phe
        195                 200                 205
Lys Val Lys Ile Asp Gln Thr Val Glu Glu Leu Arg Arg Ser Leu Ala
210                 215                 220
Pro Tyr Ala Gln Asp Thr Gln Glu Lys Leu Asn His Gln Leu Glu Gly
225                 230                 235                 240
Leu Thr Phe Gln Met Lys Lys Asn Ala Glu Glu Leu Lys Ala Arg Ile
                245                 250                 255
Ser Ala Ser Ala Glu Glu Leu Arg Gln Arg Leu Ala Pro Leu Ala Glu
            260                 265                 270
Asp Ala Arg Gly Asn Leu Lys Gly Asn Thr Glu Gly Leu Gln Lys Ser
        275                 280                 285
Leu Ala Glu Leu Gly Gly His Leu Asp Gln Gln Val Glu Glu Phe Arg
290                 295                 300
Arg Arg Val Glu Pro Tyr Gly Glu Asn Phe Asn Lys Ala Leu Val Gln
305                 310                 315                 320
Gln Met Glu Gln Leu Arg Gln Lys Leu Gly Pro His Ala Gly Asp Val
                325                 330                 335

```
Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 23
<211> LENGTH: 396
<212> TYPE: PRT
<213> ORGANISM: Homo sapiens

<400> SEQUENCE: 23

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Gln Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320
```

```
Gln Met Glu Gln Leu Arg Gln Lys Leu Gly Pro His Ala Gly Asp Val
            325                 330                 335

Glu Gly His Leu Ser Phe Leu Glu Lys Asp Leu Arg Asp Lys Val Asn
        340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
        370                 375                 380

Gln Glu Gln Val Gln Met Leu Ala Pro Leu Glu Ser
385                 390                 395

<210> SEQ ID NO 24
<211> LENGTH: 396
<212> TYPE: PRT
<213> ORGANISM: Homo sapiens

<400> SEQUENCE: 24

Met Phe Leu Lys Ala Val Val Leu Thr Leu Ala Leu Val Ala Val Ala
 1               5                  10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Thr Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
```

```
              290                 295                 300
Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
                340                 345                 350

Ser Phe Phe Ser Thr Phe Lys Glu Lys Glu Ser Gln Asp Lys Thr Leu
                355                 360                 365

Ser Leu Pro Glu Leu Glu Gln Gln Gln Glu Gln Gln Gln Glu Gln Gln
                370                 375                 380

Gln Glu Gln Val Gln Met Leu Ala Pro Leu Glu Ser
385                 390                 395
```

<210> SEQ ID NO 25
<211> LENGTH: 396
<212> TYPE: PRT
<213> ORGANISM: Homo sapiens

<400> SEQUENCE: 25

```
Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
                35                  40                  45

Leu Gln Lys Ser Glu Leu Thr Gln Gln Leu Asn Ala Leu Phe Gln Asp
50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
                100                 105                 110

Leu Leu Pro His Ala Asn Glu Val Ser Gln Lys Ile Gly Asp Asn Leu
                115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
                180                 185                 190

Asn Val Glu Glu Leu Lys Gly Arg Leu Thr Pro Tyr Ala Asp Glu Phe
                195                 200                 205

Lys Val Lys Ile Asp Gln Thr Val Glu Glu Leu Arg Arg Ser Leu Ala
                210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Lys Glu Leu Lys Ala Arg Ile
                245                 250                 255

Ser Ala Ser Ala Glu Glu Leu Arg Gln Arg Leu Ala Pro Leu Ala Glu
                260                 265                 270
```

Asp Val Arg Gly Asn Leu Lys Gly Asn Thr Glu Gly Leu Gln Lys Ser
                275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Glu Gln Gln Gln Gln Gln Gln Gln
            370                 375                 380

Gln Glu Gln Val Gln Met Leu Ala Pro Leu Glu Ser
385                 390                 395

<210> SEQ ID NO 26
<211> LENGTH: 396
<212> TYPE: PRT
<213> ORGANISM: Homo sapiens

<400> SEQUENCE: 26

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Ser His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
                260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
        290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395

<210> SEQ ID NO 27
<211> LENGTH: 396
<212> TYPE: PRT
<213> ORGANISM: Homo sapiens

<400> SEQUENCE: 27

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Lys Glu Lys Leu Asn His Gln Leu Glu Gly

```
              225                 230                 235                 240

Leu Thr Phe Gln Met Lys Lys Asn Ala Glu Glu Leu Lys Ala Arg Ile
                    245                 250                 255

Ser Ala Ser Ala Glu Glu Leu Arg Gln Arg Leu Ala Pro Leu Ala Glu
                260                 265                 270

Asp Val Arg Gly Asn Leu Lys Gly Asn Thr Glu Gly Leu Gln Lys Ser
                275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                    325                 330                 335

Glu Gly His Leu Ser Phe Leu Glu Lys Asp Leu Arg Asp Lys Val Asn
                340                 345                 350

Ser Phe Phe Ser Thr Phe Lys Glu Lys Glu Ser Gln Asp Lys Thr Leu
                355                 360                 365

Ser Leu Pro Glu Leu Glu Gln Gln Gln Glu Gln Gln Gln Glu Gln Gln
            370                 375                 380

Gln Glu Gln Val Gln Met Leu Ala Pro Leu Glu Ser
385                 390                 395

<210> SEQ ID NO 28
<211> LENGTH: 396
<212> TYPE: PRT
<213> ORGANISM: Homo sapiens

<400> SEQUENCE: 28

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
                35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
                100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
        130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
                180                 185                 190

Asn Val Glu Glu Leu Lys Gly Arg Leu Thr Pro Tyr Ala Asp Glu Phe
            195                 200                 205
```

```
Lys Val Lys Ile Asp Gln Thr Val Glu Glu Leu Cys Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
                275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
                340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 29
<211> LENGTH: 396
<212> TYPE: PRT
<213> ORGANISM: Homo sapiens

<400> SEQUENCE: 29

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190
```

-continued

Asn Val Glu Glu Leu Lys Gly Arg Leu Thr Pro Tyr Ala Asp Glu Phe
            195                 200                 205

Lys Val Lys Ile Asp His Thr Val Glu Glu Leu Arg Arg Ser Leu Ala
        210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 30
<211> LENGTH: 396
<212> TYPE: PRT
<213> ORGANISM: Homo sapiens

<400> SEQUENCE: 30

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln

```
                165                 170                 175
Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Lys Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395

<210> SEQ ID NO 31
<211> LENGTH: 396
<212> TYPE: PRT
<213> ORGANISM: Homo sapiens

<400> SEQUENCE: 31

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140
```

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Met Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395

<210> SEQ ID NO 32
<211> LENGTH: 396
<212> TYPE: PRT
<213> ORGANISM: Homo sapiens

<400> SEQUENCE: 32

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
            130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Cys Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 33
<211> LENGTH: 396
<212> TYPE: PRT
<213> ORGANISM: Homo sapiens

<400> SEQUENCE: 33

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg 100                 105                 110
Leu Leu Pro His Ala Asn Glu Val Ser Gln Lys Ile Gly Asp Asn Leu
            115                 120                 125
Arg Glu Leu Gln Gln Arg Leu Glu Pro Tyr Ala Asp Gln Leu Arg Thr
        130                 135                 140
Gln Val Asn Thr Gln Ala Glu Gln Leu Arg Arg Gln Leu Asp Pro Leu
145                 150                 155                 160
Ala Gln Arg Met Glu Arg Val Leu Arg Glu Asn Ala Asp Ser Leu Gln
                165                 170                 175
Ala Ser Leu Arg Pro His Ala Asp Glu Leu Lys Ala Lys Ile Asn Gln
            180                 185                 190
Asn Val Glu Glu Leu Lys Gly Arg Leu Thr Pro Tyr Ala Asp Glu Phe
        195                 200                 205
Lys Val Lys Ile Asp Gln Thr Val Glu Glu Leu Arg Arg Ser Leu Ala
210                 215                 220
Pro Tyr Ala Gln Asp Thr Gln Glu Lys Leu Asn His Gln Leu Glu Gly
225                 230                 235                 240
Leu Thr Phe Gln Met Lys Lys Asn Ala Glu Glu Leu Lys Ala Arg Ile
                245                 250                 255
Ser Ala Ser Ala Glu Glu Leu Arg Gln Arg Leu Ala Pro Leu Ala Glu
            260                 265                 270
Asp Val Arg Gly Asn Leu Lys Gly Asn Thr Glu Gly Leu Gln Lys Ser
        275                 280                 285
Leu Ala Glu Leu Gly Gly His Leu Asp Gln Gln Val Glu Glu Phe Arg
    290                 295                 300
Arg Arg Val Glu Pro Tyr Gly Glu Asn Phe Asn Lys Ala Leu Val Gln
305                 310                 315                 320
Gln Met Glu Gln Leu Arg Gln Lys Leu Gly Pro His Ala Gly Asp Val
                325                 330                 335
Glu Gly His Leu Ser Phe Leu Glu Lys Asp Leu Arg Asp Lys Val Asn
            340                 345                 350
Ser Phe Phe Ser Thr Phe Lys Glu Lys Glu Ser Gln Asp Lys Thr Leu
        355                 360                 365
Ser Leu Pro Glu Leu Glu Gln Gln Gln Glu Gln Gln Gln Glu Gln Gln
370                 375                 380
Gln Glu Gln Val Gln Met Leu Ala Pro Leu Glu Ser
385                 390                 395

<210> SEQ ID NO 34
<211> LENGTH: 396
<212> TYPE: PRT
<213> ORGANISM: Homo sapiens

<400> SEQUENCE: 34

Met Phe Leu Lys Ala Val Val Leu Thr Leu Ala Leu Val Ala Val Ala
1               5                   10                  15
Gly Ala Arg Ala Glu Val Ser Ala Asp Gln Val Ala Thr Val Met Trp
                20                  25                  30
Asp Tyr Phe Ser Gln Leu Ser Asn Asn Ala Lys Glu Ala Val Glu His
            35                  40                  45
Leu Gln Lys Ser Glu Leu Thr Gln Gln Leu Asn Ala Leu Phe Gln Asp
        50                  55                  60
Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                    85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
        130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asn Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Glu Gln Gln
370                 375                 380

Gln Glu Gln Val Gln Met Leu Ala Pro Leu Glu Ser
385                 390                 395

<210> SEQ ID NO 35
<211> LENGTH: 396
<212> TYPE: PRT
<213> ORGANISM: Homo sapiens

<400> SEQUENCE: 35

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
        130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Leu His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Gln Gln Gln Gln Glu Gln Gln
370                 375                 380

Gln Glu Gln Val Gln Met Leu Ala Pro Leu Glu Ser
385                 390                 395

<210> SEQ ID NO 36
<211> LENGTH: 396
<212> TYPE: PRT
<213> ORGANISM: Homo sapiens

<400> SEQUENCE: 36

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His

```
                35                  40                  45
Leu Gln Lys Ser Glu Leu Thr Gln Gln Leu Asn Ala Leu Phe Gln Asp
 50                  55                  60
Lys Leu Gly Glu Val Asn Thr Tyr Ala Gly Asp Leu Gln Lys Lys Leu
 65                  70                  75                  80
Val Pro Phe Ala Thr Glu Leu His Glu Arg Leu Ala Lys Asp Ser Glu
                 85                  90                  95
Lys Leu Lys Glu Glu Ile Gly Lys Glu Leu Glu Glu Leu Arg Ala Arg
            100                 105                 110
Leu Leu Pro His Ala Asn Glu Val Ser Gln Lys Ile Gly Asp Asn Leu
        115                 120                 125
Arg Glu Leu Gln Gln Arg Leu Glu Pro Tyr Ala Asp Gln Leu Arg Thr
130                 135                 140
Gln Val Asn Thr Gln Ala Glu Gln Leu Arg Arg Gln Leu Asp Pro Leu
145                 150                 155                 160
Ala Gln Arg Met Glu Arg Val Leu Arg Glu Asn Thr Asp Ser Leu Gln
                165                 170                 175
Ala Ser Leu Arg Pro His Ala Asp Glu Leu Lys Ala Lys Ile Asp Gln
            180                 185                 190
Asn Val Glu Glu Leu Lys Gly Arg Leu Thr Pro Tyr Ala Asp Glu Phe
        195                 200                 205
Lys Val Lys Ile Asp Gln Thr Val Glu Glu Leu Arg Arg Ser Leu Ala
210                 215                 220
Pro Tyr Ala Gln Asp Thr Gln Glu Lys Leu Asn His Gln Leu Glu Gly
225                 230                 235                 240
Leu Thr Phe Gln Met Lys Lys Asn Ala Glu Glu Leu Lys Ala Arg Ile
                245                 250                 255
Ser Ala Ser Ala Glu Glu Leu Arg Gln Arg Leu Ala Pro Leu Ala Glu
            260                 265                 270
Asp Val Arg Gly Asn Leu Lys Gly Asn Thr Glu Gly Leu Gln Lys Ser
        275                 280                 285
Leu Ala Glu Leu Gly Gly His Leu Asp Gln Gln Val Glu Glu Phe Arg
290                 295                 300
Arg Arg Val Glu Pro Tyr Gly Glu Asn Phe Asn Lys Ala Leu Val Gln
305                 310                 315                 320
Gln Met Glu Gln Leu Arg Gln Lys Leu Gly Pro His Ala Gly Asp Val
                325                 330                 335
Glu Gly His Leu Ser Phe Leu Glu Lys Asp Leu Arg Asp Lys Val Asn
            340                 345                 350
Ser Phe Phe Ser Thr Phe Lys Glu Lys Glu Ser Gln Asp Lys Thr Leu
        355                 360                 365
Ser Leu Pro Glu Leu Glu Gln Gln Gln Glu Gln Gln Gln Glu Gln Gln
    370                 375                 380
Gln Glu Gln Val Gln Met Leu Ala Pro Leu Glu Ser
385                 390                 395

<210> SEQ ID NO 37
<211> LENGTH: 396
<212> TYPE: PRT
<213> ORGANISM: Homo sapiens

<400> SEQUENCE: 37

Met Phe Leu Lys Ala Val Val Leu Thr Leu Ala Leu Val Ala Val Ala
  1               5                  10                  15
```

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
50                      55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
        130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Trp Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 38
<211> LENGTH: 396
<212> TYPE: PRT
<213> ORGANISM: Homo sapiens

<400> SEQUENCE: 38

```
Met Phe Leu Lys Ala Val Val Leu Thr Leu Ala Leu Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ser Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 39
<211> LENGTH: 396
```

<212> TYPE: PRT
<213> ORGANISM: Homo sapiens

<400> SEQUENCE: 39

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Trp Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 40
<211> LENGTH: 396
<212> TYPE: PRT
<213> ORGANISM: Homo sapiens

<400> SEQUENCE: 40

```
Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Met Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
```

```
            370                 375                 380
Gln Glu Gln Val Gln Met Leu Ala Pro Leu Glu Ser
385                 390                 395

<210> SEQ ID NO 41
<211> LENGTH: 396
<212> TYPE: PRT
<213> ORGANISM: Homo sapiens

<400> SEQUENCE: 41

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Ser Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350
```

```
Ser Phe Phe Ser Thr Phe Lys Glu Lys Glu Ser Gln Asp Lys Thr Leu
                355                 360                 365

Ser Leu Pro Glu Leu Glu Gln Gln Gln Glu Gln Gln Glu Gln Gln Gln
    370                 375                 380

Gln Glu Gln Val Gln Met Leu Ala Pro Leu Glu Ser
385                 390                 395

<210> SEQ ID NO 42
<211> LENGTH: 396
<212> TYPE: PRT
<213> ORGANISM: Homo sapiens

<400> SEQUENCE: 42

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
                35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
                100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Glu Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335
```

-continued

```
Glu Gly His Leu Ser Phe Leu Glu Lys Asp Leu Arg Asp Lys Val Asn
                340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
        370                 375                 380

Gln Glu Gln Val Gln Met Leu Ala Pro Leu Glu Ser
385                 390                 395

<210> SEQ ID NO 43
<211> LENGTH: 396
<212> TYPE: PRT
<213> ORGANISM: Homo sapiens

<400> SEQUENCE: 43

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Lys Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
```

```
                305                 310                 315                 320
Gln Met Glu Gln Leu Arg Gln Lys Leu Gly Pro His Ala Gly Asp Val
                325                 330                 335
Glu Gly His Leu Ser Phe Leu Glu Lys Asp Leu Arg Asp Lys Val Asn
                340                 345                 350
Ser Phe Phe Ser Thr Phe Lys Glu Lys Glu Ser Gln Asp Lys Thr Leu
                355                 360                 365
Ser Leu Pro Glu Leu Glu Gln Gln Gln Glu Gln Gln Gln Gln Gln Gln
                370                 375                 380
Gln Glu Gln Val Gln Met Leu Ala Pro Leu Glu Ser
385                 390                 395

<210> SEQ ID NO 44
<211> LENGTH: 396
<212> TYPE: PRT
<213> ORGANISM: Homo sapiens

<400> SEQUENCE: 44

Met Phe Leu Lys Ala Val Val Leu Thr Leu Ala Leu Val Ala Val Ala
1               5                   10                  15
Gly Ala Arg Ala Glu Val Ser Ala Asp Gln Val Ala Thr Val Met Trp
                20                  25                  30
Asp Tyr Phe Ser Gln Leu Ser Asn Asn Ala Lys Glu Ala Val Glu His
                35                  40                  45
Leu Gln Lys Ser Glu Leu Thr Gln Gln Leu Asn Ala Leu Phe Gln Asp
                50                  55                  60
Lys Leu Gly Glu Val Asn Thr Tyr Ala Gly Asp Leu Gln Lys Lys Leu
65                  70                  75                  80
Val Pro Phe Ala Thr Glu Leu His Glu Arg Leu Ala Lys Asp Leu Glu
                85                  90                  95
Lys Leu Lys Glu Glu Ile Gly Lys Glu Leu Glu Glu Leu Arg Ala Arg
                100                 105                 110
Leu Leu Pro His Ala Asn Glu Val Ser Gln Lys Ile Gly Asp Asn Leu
                115                 120                 125
Arg Glu Leu Gln Gln Arg Leu Glu Pro Tyr Ala Asp Gln Leu Arg Thr
                130                 135                 140
Gln Val Asn Thr Gln Ala Glu Gln Leu Arg Arg Gln Leu Asp Pro Leu
145                 150                 155                 160
Ala Gln Arg Met Glu Arg Val Leu Arg Glu Asn Ala Asp Ser Leu Gln
                165                 170                 175
Ala Ser Leu Arg Pro His Ala Asp Glu Leu Lys Ala Lys Ile Asp Gln
                180                 185                 190
Asn Val Glu Glu Leu Lys Gly Arg Leu Thr Pro Tyr Ala Asp Glu Phe
                195                 200                 205
Lys Val Lys Ile Asp Gln Thr Val Glu Glu Leu Arg Arg Ser Leu Ala
                210                 215                 220
Pro Tyr Ala Gln Asp Thr Gln Glu Lys Leu Asn His Gln Leu Glu Gly
225                 230                 235                 240
Leu Thr Phe Gln Met Lys Lys Asn Ala Glu Glu Leu Lys Ala Arg Ile
                245                 250                 255
Ser Ala Ser Ala Glu Glu Leu Arg Gln Arg Leu Ala Pro Leu Ala Glu
                260                 265                 270
Asp Val Arg Gly Asn Leu Lys Gly Asn Thr Glu Gly Leu Gln Lys Ser
                275                 280                 285
```

Leu Ala Glu Leu Gly Gly His Leu Asp Gln Gln Val Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
            325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Gln Gln Gln
370                 375                 380

Gln Glu Gln Val Gln Met Leu Ala Pro Leu Glu Ser
385                 390                 395

<210> SEQ ID NO 45
<211> LENGTH: 396
<212> TYPE: PRT
<213> ORGANISM: Homo sapiens

<400> SEQUENCE: 45

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Cys Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

-continued

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
        290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
370                 375                 380

Gln Glu Gln Val Gln Met Leu Ala Pro Leu Glu Ser
385                 390                 395

<210> SEQ ID NO 46
<211> LENGTH: 396
<212> TYPE: PRT
<213> ORGANISM: Homo sapiens

<400> SEQUENCE: 46

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Ala Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile

```
                        245                 250                 255
Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
            325                 330                 335

Glu Gly His Leu Ser Phe Leu Glu Lys Asp Leu Arg Asp Lys Val Asn
        340                 345                 350

Ser Phe Phe Ser Thr Phe Lys Glu Lys Glu Ser Gln Asp Lys Thr Leu
    355                 360                 365

Ser Leu Pro Glu Leu Glu Gln Gln Gln Glu Gln Gln Gln Gln Gln Gln
370                 375                 380

Gln Glu Gln Val Gln Met Leu Ala Pro Leu Glu Ser
385                 390                 395

<210> SEQ ID NO 47
<211> LENGTH: 396
<212> TYPE: PRT
<213> ORGANISM: Homo sapiens

<400> SEQUENCE: 47

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu His Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220
```

```
Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
            245                 250                 255

Ser Ala Ser Ala Glu Glu Leu Arg Gln Arg Leu Ala Pro Leu Ala Glu
        260                 265                 270

Asp Val Arg Gly Asn Leu Lys Gly Asn Thr Glu Gly Leu Gln Lys Ser
    275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
            325                 330                 335

Glu Gly His Leu Ser Phe Leu Glu Lys Asp Leu Arg Asp Lys Val Asn
        340                 345                 350

Ser Phe Phe Ser Thr Phe Lys Glu Lys Glu Ser Gln Asp Lys Thr Leu
    355                 360                 365

Ser Leu Pro Glu Leu Glu Gln Gln Gln Glu Gln Gln Gln Gln Gln Gln
370                 375                 380

Gln Glu Gln Val Gln Met Leu Ala Pro Leu Glu Ser
385                 390                 395

<210> SEQ ID NO 48
<211> LENGTH: 396
<212> TYPE: PRT
<213> ORGANISM: Homo sapiens

<400> SEQUENCE: 48

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Ser Asp Leu Gln Lys Lys Leu
65                  70                  75                  80

Val Pro Phe Ala Thr Glu Leu His Glu Arg Leu Ala Lys Asp Ser Glu
            85                  90                  95

Lys Leu Lys Glu Glu Ile Gly Lys Glu Leu Glu Glu Leu Arg Ala Arg
        100                 105                 110

Leu Leu Pro His Ala Asn Glu Val Ser Gln Lys Ile Gly Asp Asn Leu
    115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
            165                 170                 175

Ala Ser Leu Arg Pro His Ala Asp Glu Leu Lys Ala Lys Ile Asp Gln
        180                 185                 190

Asn Val Glu Glu Leu Lys Gly Arg Leu Thr Pro Tyr Ala Asp Glu Phe
    195                 200                 205
```

Lys Val Lys Ile Asp Gln Thr Val Glu Glu Leu Arg Arg Ser Leu Ala
            210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
            245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
            325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Gln Gln Gln
370                 375                 380

Gln Glu Gln Val Gln Met Leu Ala Pro Leu Glu Ser
385                 390                 395

<210> SEQ ID NO 49
<211> LENGTH: 396
<212> TYPE: PRT
<213> ORGANISM: Homo sapiens

<400> SEQUENCE: 49

Met Phe Leu Lys Ala Val Val Leu Thr Leu Ala Leu Met Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
            85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
            165                 170                 175

Ala Ser Leu Arg Pro His Ala Asp Glu Leu Lys Ala Lys Ile Asp Gln

```
            180                 185                 190
Asn Val Glu Glu Leu Lys Gly Arg Leu Thr Pro Tyr Ala Asp Glu Phe
            195                 200                 205
Lys Val Lys Ile Asp Gln Thr Val Glu Glu Leu Arg Arg Ser Leu Ala
            210                 215                 220
Pro Tyr Ala Gln Asp Thr Gln Glu Lys Leu Asn His Gln Leu Glu Gly
225                 230                 235                 240
Leu Thr Phe Gln Met Lys Lys Asn Ala Glu Glu Leu Lys Ala Arg Ile
                245                 250                 255
Ser Ala Ser Ala Glu Glu Leu Arg Gln Arg Leu Ala Pro Leu Ala Glu
                260                 265                 270
Asp Val Arg Gly Asn Leu Lys Gly Asn Thr Glu Gly Leu Gln Lys Ser
                275                 280                 285
Leu Ala Glu Leu Gly Gly His Leu Asp Gln Gln Val Glu Glu Phe Arg
                290                 295                 300
Arg Arg Val Glu Pro Tyr Gly Glu Asn Phe Asn Lys Ala Leu Val Gln
305                 310                 315                 320
Gln Met Glu Gln Leu Arg Gln Lys Leu Gly Pro His Ala Gly Asp Val
                325                 330                 335
Glu Gly His Leu Ser Phe Leu Glu Lys Asp Leu Arg Asp Lys Val Asn
                340                 345                 350
Ser Phe Phe Ser Thr Phe Lys Glu Lys Glu Ser Gln Asp Lys Thr Leu
                355                 360                 365
Ser Leu Pro Glu Leu Glu Gln Gln Gln Glu Gln Gln Gln Glu Gln Gln
                370                 375                 380
Gln Glu Gln Val Gln Met Leu Ala Pro Leu Glu Ser
385                 390                 395

<210> SEQ ID NO 50
<211> LENGTH: 396
<212> TYPE: PRT
<213> ORGANISM: Homo sapiens

<400> SEQUENCE: 50

Met Phe Leu Lys Ala Met Val Leu Thr Leu Ala Leu Val Ala Val Ala
1               5                   10                  15
Gly Ala Arg Ala Glu Val Ser Ala Asp Gln Val Ala Thr Val Met Trp
                20                  25                  30
Asp Tyr Phe Ser Gln Leu Ser Asn Asn Ala Lys Glu Ala Val Glu His
                35                  40                  45
Leu Gln Lys Ser Glu Leu Thr Gln Gln Leu Asn Ala Leu Phe Gln Asp
        50                  55                  60
Lys Leu Gly Glu Val Asn Thr Tyr Ala Gly Asp Leu Gln Lys Lys Leu
65                  70                  75                  80
Val Pro Phe Ala Thr Glu Leu His Glu Arg Leu Ala Lys Asp Ser Glu
                85                  90                  95
Lys Leu Lys Glu Glu Ile Gly Lys Glu Leu Glu Glu Leu Arg Ala Arg
                100                 105                 110
Leu Leu Pro His Ala Asn Glu Val Ser Gln Lys Ile Gly Asp Asn Leu
                115                 120                 125
Arg Glu Leu Gln Gln Arg Leu Glu Pro Tyr Ala Asp Gln Leu Arg Thr
        130                 135                 140
Gln Val Asn Thr Gln Ala Glu Gln Leu Arg Arg Gln Leu Asp Pro Leu
145                 150                 155                 160
```

```
Ala Gln Arg Met Glu Arg Val Leu Arg Glu Asn Ala Asp Ser Leu Gln
            165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
275                 280                 285

Leu Ala Glu Leu Gly Gly His Leu Asp Gln Gln Val Glu Glu Phe Arg
            290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
            355                 360                 365

Ser Leu Pro Glu Leu Glu Gln Gln Gln Glu Gln Gln Gln Glu Gln Gln
            370                 375                 380

Gln Glu Gln Val Gln Met Leu Ala Pro Leu Glu Ser
385                 390                 395

<210> SEQ ID NO 51
<211> LENGTH: 396
<212> TYPE: PRT
<213> ORGANISM: Homo sapiens

<400> SEQUENCE: 51

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
```

```
                130               135              140
Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
                180                 185                 190

Asn Val Glu Glu Leu Lys Gly Arg Leu Thr Pro Tyr Ala Asp Glu Phe
                195                 200                 205

Lys Val Lys Ile Asp Gln Thr Val Glu Glu Leu Arg Arg Ser Leu Ala
                210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
                260                 265                 270

Asp Val Arg Gly Asn Leu Lys Gly Asn Thr Glu Gly Leu Gln Lys Ser
                275                 280                 285

Leu Ala Glu Leu Gly Gly His Leu Asp Gln Gln Val Glu Glu Phe Arg
290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
                340                 345                 350

Ser Phe Phe Ser Thr Phe Lys Glu Lys Glu Ser Gln Asp Lys Thr Leu
                355                 360                 365

Ser Leu Pro Glu Leu Glu Gln Gln Gln Glu Gln Gln Gln Glu Gln Gln
                370                 375                 380

Gln Glu Gln Val Gln Met Leu Ala Pro Leu Glu Ser
385                 390                 395
```

What is claimed is:

1. A method of lowering blood glucose level in a subject having a hyperglycemia disorder, the method comprising administering to the subject an effective amount of an apolipoprotein A-IV protein consisting of amino acid sequence (SEQ ID NO. 4)

$X_1$EVSADQVATVMWDYFSQLSNNAKEAVEHLQKSELTQQLNALFQD

KLGEVNTYAGDLQKKLVPFATELHERLAKDSEKLKEEIGKELEELRARLL

PHANEVSQKIGDNLRELQQRLEPYADQLRTQVNTQAEQLRRQLTPYAQRM

ERVLRENADSLQASLRPHAD$X_2$LKAKIDQNVEELKGRLTPYADEFKVKID

QTVEELRRSLAPYAQDTQEKLNHQLEGLTFQMKKNAEELKARISASAEEL

RQRLAPLAEDVRGNLRGNTEGLQKSLAELGGHLDQQVEEFRRRVEPYGEN

FNKALVQQMEQLRQKLGPHAGDVEGHLSFLEKDLRDKVNSFFSTFKEKES

QDK$X_3$LSLPELEQQQEQ$X_4$QEQQQEQVQMLAPLES wherein, $X_1$ must be present and is G, A, or V;

$X_2$ is E or K;

$X_3$ is T or S; and $X_4$ is Q or H.

2. The method of claim 1, wherein the hyperglycemic disorder is an insulin resistant disorder or an endocrine disorder associated with hyperglycemia.

3. The method of claim 2, wherein the insulin resistant disorder is selected from the group consisting of prediabetes, metabolic syndrome, polycystic ovary disease, type A syndrome, and gestational diabetes.

4. A method for treating a hyperglycemic disorder in a subject in need thereof, the method comprising administering to the subject an effective amount of an apolipoprotein A-IV protein consisting of amino acid sequence (SEQ ID NO. 4)

$X_1$EVSADQVATVMWDYFSQLSNNAKEAVEHLQKSELTQQLNALFQD

KLGEVNTYAGDLQKKLVPFATELHERLAKDSEKLKEEIGKELEELRARLL

-continued

PHANEVSQKIGDNLRELQQRLEPYADQLRTQVNTQAEQLRRQLTPYAQRM

ERVLRENADSLQASLRPHADX₂LKAKIDQNVEELKGRLTPYADEFKVKID

QTVEELRRSLAPYAQDTQEKLNHQLEGLTFQMKKNAEELKARISASAEEL

RQRLAPLAEDVRGNLRGNTEGLQKSLAELGGHLDQQVEEFRRRVEPYGEN

FNKALVQQMEQLRQKLGPHAGDVEGHLSFLEKDLRDKVNSFFSTFKEKES

QDKX₃LSLPELEQQQEQX₄QEQQQEQVQMLAPLES wherein, $X_1$ must be present and is G, A, or V;
$X_2$ is E or K;
$X_3$ is T or S; and
$X_4$ is Q or H.

5. The method of claim 4, wherein the amino acid sequence of the apolipoprotein A-IV protein is (SEQ ID NO. 3)
GEVSADQVATVMWDYFSQLSNNAKEAVEHLQKSELTQQLNALFQDK

LGEVNTYAGDLQKKLVPFATELHERLAKDSEKLKEEIGKELEELRARLLP

HANEVSQKIGDNLRELQQRLEPYADQLRTQVNTQAEQLRRQLTPYAQRME

RVLRENADSLQASLRPHADELKAKIDQNVEELKGRLTPYADEFKVKIDQT

VEELRRSLAPYAQDTQEKLNHQLEGLTFQMKKNAEELKARISASAEELRQ

RLAPLAEDVRGNLRGNTEGLQKSLAELGGHLDQQVEEFRRRVEPYGENFN

KALVQQMEQLRQKLGPHAGDVEGHLSFLEKDLRDKVNSFFSTFKEKESQD

KTLSLPELEQQQEQQQEQQQEQVQMLAPLES.

6. The method of claim 4, wherein the apolipoprotein A-IV protein is administered systemically and the systemic administration is selected from the group consisting of oral, subcutaneous, intravenous, intramuscular, and intraperitoneal administration.

7. The method of claim 4, wherein the apolipoprotein A-IV protein is administered in a dose of about 1 to about 10 μg/g.

8. The method of claim 4, wherein the apolipoprotein A-IV protein is administered in a dose of about 0.25 to about 2 μg/g.

9. The method of claim 4, wherein the apolipoprotein A-IV protein is administered in a dose of about 1 μg/g.

10. The method of claim 4, wherein the apolipoprotein A-IV protein is administered once daily.

* * * * *